US009078429B2

(12) United States Patent
McGann et al.

(10) Patent No.: US 9,078,429 B2
(45) Date of Patent: Jul. 14, 2015

(54) METHOD OF CRYOPRESERVING STEM CELLS

(75) Inventors: Locksley Earl McGann, Spruce Grove (CA); Janet Anne Wade Elliott, Edmonton (CA); Lisa Ula Ross-Rodriguez, St. Albert (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 584 days.

(21) Appl. No.: 12/656,600

(22) Filed: Feb. 4, 2010

(65) Prior Publication Data

US 2010/0240127 A1   Sep. 23, 2010

Related U.S. Application Data

(63) Continuation of application No. 11/228,388, filed on Sep. 19, 2005, now abandoned.

(60) Provisional application No. 60/611,391, filed on Sep. 18, 2004.

(30) Foreign Application Priority Data

Sep. 17, 2004   (CA) ..................................... 2482045

(51) Int. Cl.
*C12N 5/00* (2006.01)
*A01N 1/02* (2006.01)

(52) U.S. Cl.
CPC ................ *A01N 1/02* (2013.01); *A01N 1/0284* (2013.01)

(58) Field of Classification Search
CPC ..................... C12N 2500/36; C12N 2501/105; C12N 2501/125; C12N 2501/14; C12N 2501/145; A01N 1/0221
See application file for complete search history.

(56) References Cited

U.S. PATENT DOCUMENTS

| | | | |
|---|---|---|---|
| 5,071,741 A | 12/1991 | Brockbank | |
| 6,361,934 B1 | 3/2002 | Acton et al. | |
| 6,365,405 B1 * | 4/2002 | Salzmann et al. | 435/366 |
| 6,740,484 B1 | 5/2004 | Khirabadi et al. | |
| 6,881,231 B2 | 4/2005 | Acton et al. | |
| 8,440,390 B2 | 5/2013 | Brockbank | |
| 2004/0053204 A1 | 3/2004 | Morris et al. | |
| 2004/0209235 A1 * | 10/2004 | Goldstein et al. | 435/1.1 |

OTHER PUBLICATIONS

Beaujean, F., et al. Successful cryopreservation of purified autologous CD34+ cells: Influence of freezing parameters on cell recovery and engraftment, Bone Marrow Transplantation, 1998, vol. 22, pp. 1091-1096.*
Ross-Rodriguez, L.U. et al. "Using simulations to design a cryopreservation procedure for hematopoietic stem cells without DMSO", Cryobiology, 2003, abstract No. 22, on p. 255 (renumbered as p. 1); and slide Presentation, renumbered as pp. 2-19.*
Rowley S.D., Cryopreservation, Storage and Shipment—ISHAGE 2001—Technical Breakfast 1 & 16, Storage and cryopreservation of cell products, published on the web at—Published on the web at: http://c.ymcdn.com/sites/www.celltherapysociety.org/resource/resmgr/files/PDF/Resources/Cryopreservation/Cryopreservation_Storage_and_Shipment.pdf, pp. 1-4.*
John Farrant et al.: Optimal Recovery of Lymphocytes and Tissue Culture Cells Following Rapid Cooling; Nature vol. 249; May 31, 1974; p. 452-453.
Jenny Foss Abrahamsen et al.: "Cryopreserving Human Peripheral Blood Progenitor Cells With 5-Percent Rather Than 10-Percent DMSO Results in Less Apoptosis and Necrosis in CD34+ Cells" Transfusion, vol. 42, No. 12; p. 1573-1580; Dec. 2002.
Pablo Rubinstein et al."Processing and Cryopreservation of Placental/Umbilical Cord Blood for Unrelated Bone Marrow Reconstitution"; Proceedings of the National Academy of Sciences, USA; vol. 92, p. 10119-10122; Oct. 1995.
R. Sharma et al: A Novel Method to Measure Cryoprotectant Permeation Into Intact Articular Cartilage; Crybiology 54: 2, 196-203; 2007.
Abrahamsen, J.F. et al. "Cryopreserving human peripheral blood progenitor cells with 5-percent rather than 10-percent DMSO results in less apoptosis and necrosis in CD34+ cells", *Transfusion*, vol. 42, p. 1573-1580 (2002).
Acker, J.P. et al. "Innocuous intracellular ice improves survival of frozen cells", *Cell Transplantation*, vol. 11, p. 563-571 (2002).
Acker, J.P. et al. "Intracellular ice propagation: Experimental evidence for ice growth through membrane pores", *Biophysical Journal*, vol. 81, p. 1389-1397 (2001).
Baust, J.M. et al. "Modulation of the cryopreservation cap: Elevated survival with reduced dimethyl sulfoxide concentration", *Cryobiology*, vol. 45, p. 97-108 (2002).
Beaujean, F., et al. "Successful cryopreservation of purified autologous CD34(+) cells: Influence of freezing parameters on cell recovery and engraftment", *Bone Marrow Transplantation*, vol. 22, p. 1091-1096 (1998).
Benson, C.T. et al. "Hydraulic conductivity (L-p) and its activation energy (E-a), cryoprotectant agent permeability (P-s) and its E-a, and reflection coefficients (sigma) for golden hamster individual pancreatic islet cell membranes", *Cryobiology*, vol. 37, p. 290-299 (1998).
Davis, J.M. et al. "Clinical toxicity of cryopreserved bone-marrow graft infusion", *Blood*, vol. 75, p. 781-786 (1990).
Diller, K.R. "Intracellular freezing: effect of extracellular supercooling", *Cryobiology*, vol. 12, p. 480-485 (1975).

(Continued)

*Primary Examiner* — Satyendra Singh
(74) *Attorney, Agent, or Firm* — Anthony R. Lambert

(57) ABSTRACT

A non-linear cooling cryopreservation method for improving cryopreservation protocols for cells that involves producing a simulation of cellular responses to a range of cooling parameters; determining optimal cooling parameters required to minimize cryoinjury to the cells using simulation of cellular responses and experimental results; and incorporating optimal parameters into the protocol. The simulation is based on mathematical models of cellular parameters. A non-linear cooling cryopreservation protocol for cryopreserving stem cells is also disclosed that does not require cryoprotectants.

4 Claims, 13 Drawing Sheets

(56) References Cited

OTHER PUBLICATIONS

Donaldson, C. et al., "Optimal cryopreservation of human umbilical cord blood", *Bone Marrow Transplantation*, vol. 18, p. 725-731 (1996).
Ebertz, S.L. "Fundamental cryobiology of cells from a bioengineered human corneal equivalent", *Doctor of Philosophy, Medical Sciences—Laboratory Medicine and Pathology, University of Alberta* (2002).
Ebertz, S.L. et al. "Osmotic parameters of cells from a bioengineered human corneal equivalent and consequences for cryopreservation", *Cryobiology*, vol. 45, p. 109-117 (2002).
Egorin, M.J. et al. "Plasma concentrations and pharmacokinetics of dimethylsulfoxide and its metabolites in patients undergoing peripheral-blood stem-cell transplants", *Journal of Clinical Oncology*, vol. 16, p. 610-615 (1998).
Elliott, J.A.W. et al. "Thermodynamics in cryobiology: Limitations of the Boyle van't Hoff equation", *Cryobiology*, vol. 45, p. 252 (2002).
Elmoazzen, H.Y. et al. Implications of dilute and non-dilute solution assumptions in osmotic transport models (Cryo 2004, Society for Cryobiology Annual Meeting, Beijing, China—Jul. 15-19, 2004), *Cryobiology*, vol. 49, p. 301 (2004).
Farrant, J. et al. "Optimal recovery of lymphocytes and tissue culture cells following rapid cooling", *Nature*, vol. 249, p. 452-452 (1974).
Farrant, J. et al. "Use of two-step cooling procedures to examine factors influencing cell survival following freezing and thawing", *Cryobiology*, vol. 14, p. 273-286 (1977).
Gao, D.Y. et al. "Fundamental cryobiology of human hematopoietic progenitor cells I: Osmotic characteristics and volume distribution", *Cryobiology*, vol. 36, p. 40-48 (1998).
Hunt, C.J. et al. "Cryopreservation of umbilical cord blood: 1. Osmotically inactive volume, hydraulic conductivity and permeability of CD34(+) cells to dimethyl sulphoxide", *Cryobiology*, vol. 46, p. 61-75 (2003).
Incropera, F.P. et al. "Introduction to heat transfer", *John Wiley & Sons, New York*, N.Y., p. 441 (2002).
Jacobs, M.H. "The simultaneous measurement of cell permeability to water and to dissolved substances", *Journal of Cellular and Comparative Physiology*, vol. 2, p. 427-444 (1933).
Katayama, Y. et al. "The effects of a simplified method for cryopreservation and thawing procedures on peripheral blood stem cells", *Bone Morrow Transplantation*, vol. 19, p. 283-287 (1997).
Kedem, O. et al. "Thermodynamic Analysis of the Permeability of Biological Membrances to Non-Electrolytes", *Biochimica et Biophysica Acta*, vol. 27, p. 229-246 (1958).
Knight, S.C. et al. "Storage of human lymphocytes by freezing in serum alone" *Cryobiology*, vol. 14, p. 112-115 (1977).
Lucke, B. et al. "The living cell as an osmotic system and its permeability to water" *Physiological Reviews*, vol. 12, p. 68-139 (1932).
Mazur, P. et al. "A two-factor hypothesis of freezing injury: Evidence from Chinese hamster tissue-culture cells", *Experimental Cell Research*, vol. 71, p. 345-355 (1972).
Mazur, P. "Role of intracellular freezing in death of cells cooled at supraoptimal rates" *Cryobiology*, vol. 14, p. 251-272 (1977).
McGann, L.E. et al. "Survival of tissue culture cells frozen by a two-step procedure to -196° C. I. Holding temperature and time" *Cryobiology*, vol. 13, p. 261-268 (1976).
McGann, L.E. "Optimal temperature ranges for control of cooling rate" *Cryobiology*, vol. 16, p. 211-216 (1979).
McGann, L.E. et al. "Cryopreservation of human peripheral blood stem cells: Optimal cooling and warming conditions", *Cyrobiology*, vol. 18, p. 469-472 (1981).
McGann, L.E. et al. "Water permeability of human hematopoietic stem cells" *Cryobiology*, vol. 24, p. 112-119 (1987).
McGann, L.E. et al. "Optimization of cryopreservation protocols using computer simulations" *Cryobiology*, vol. 47, p. 255 (2003).
McGrath, J.J. "Membrane transport properties" in: Diller, K.R.(Ed), Low Temperature Biotechnology: Emerging applications and engineering contributions (American Society of Mechanical Engineers, New York, N.Y.), p. 273-330 (1988).
Morris, G.J. et al. "A novel approach to sperm cryopreservation" *Human Reproduction*, vol. 14, p. 1013-1021 (1999).
Muldrew, K. et al. "Mechanisms of intracellular ice formation" *Biophysical Journal*, vol. 57, p. 525-532 (1990).
Novikov, A.N. et al. "Possible use of exponential regimens of cooling in biological cryopreservation" *Biofizika*, vol. 30, p. 1042-1045 (1985).
Ross-Rodriguez, L.U. "Using simulations to design a cryopreservation procedure for hematopoietic stem cells without DMSO (Masters of Science, Medical Sciences-Laboratory Medicine and Pathology, University of Alberta)" Thesis (2004).
Ross-Rodriguez, L.U. et al. "Using simulations to design a cryopreservation procedure for hematopoietic stem cells without DMSO" CRYO 2003.
Sakai, A. "Survival of plant tissue at super-low temperatures III. Relation between effective pre-freezing temperatures and the degree of frost hardiness", *Plant Physiology*, vol. 40, p. 882-887 (1965).
Santos, N. C. et al. "Multidisciplinary utilization of dimethyl sulfoxide: Pharmacological, cellular and molecular aspects", *Biochemical Pharmacology*, vol. 65, p. 1035-1041 (2003).
Shabana, M. et al. "Cryomicroscope investigation and thermodynamic modeling of the freezing of unfertilized hamster ova", *Cryobiology*, vol. 25, p. 228-254 (1988).
Toner, M. et al. "Cellular response of mouse oocytes to freezing stress: prediction of intracellular ice formation", *J. of Biomechanical Engineering—Transactions of the Asme*, vol. 115, p. 169-174 (1993).
Voet, D. et al. "Biochemistry", *John Wiley & Sons, New York*, NY, p. 288-289 (1995).
Woelders, H. et al. "Theoretical prediction of 'optimal' freezing programmes", *Cryobiology*, vol. 49, p. 258-271 (2004).
Woods, E.J. et al. "Osmometric and permeability characteristics of human placental/umbilical cord blood CD34 (+) cells and their application to cryopreservation", *J. of Hematotherapy & Stem Cell Research* (now called Stem Cells & Development), vol. 9, p. 161-173 (2000).
Woods, E.J. et al. "Water and cryoprotectant permeability characteristics of isolated human and canine pancreatic islets", *Cell Transplantation*, vol. 8, p. 549-559 (1999).
Yang, H. et al. "In situ assessment of cell viability", *Cell Transplantation*, vol. 7, p. 443-451 (1998).
Yang, H. et al. "Effects of incubation temperature and time after thawing on viability assessment of peripheral hematopoietic progenitor cells cryopreserved for transplantation", *Bone Marrow Transplantation*, vol. 32, p. 1021-1026 (2003).
Zambelli, A. et al. "Clinical toxicity of cryopreserved circulating progenitor cells infusion", *Anticancer Research*, vol. 18, p. 4705-4708 (1998).

* cited by examiner

METHOD OF CRYOPRESERVING STEM CELLS

RELATED APPLICATIONS

This application is a continuation application of U.S. patent application Ser. No. 11/228,388 filed Sep. 19, 2005 entitled "Method of Cryopreserving Cells", which claims priority from U.S. Provisional Patent Application No. 60/611, 391 entitled "Method of Cryopreserving Cells", having a current filing date of Sep. 18, 2004, but for which a petition was filed to correct the filing date to Sep. 17, 2004; and to Canadian Patent Application Number 2,482,045, also entitled "Method of Cryopreserving Cells", filed Sep. 17, 2004. All of such references are herein incorporated by reference.

TECHNICAL FIELD

This application relates to methods of cryopreservation, particularly methods of cryopreserving cells and tissues.

BACKGROUND

Cryobiology is the study of the effects of low temperatures on biological systems. Although freezing is lethal to most living systems, cryobiologists have been able to preserve cells and tissues at a range of subzero temperatures, as low as liquid nitrogen temperatures (−196° C.). Currently, cryoprotection can be applied to most cells in suspension, such as stem cells, other progenitor cells, red and white blood cells, sperm cells, oocytes, ova, and cellular materials derived from tissues and organs (including but not limited to pancreatic islet cells, chondrocytes, cells of neural origin, cells of hepatic origin, cells of opthalmolic origin, cells of orthopedic origin, cells from connective tissues, cells of reproductive origin, and cells of cardiac origin). Cryopreservation has also been used to effectively preserve tissue, such as heart valves, embryos, skin, articular cartilage, and islets of Langerhans and an increasing range of engineered tissues and tissue constructs. Although the current recovery of viable cells post-thaw may be sufficient for some clinical uses, recovery is generally considered less than optimal due to injury during the freezing process.

Cryopreservation has been applied to many cell and tissue types. Recent developments in the utilization of a variety of stem cells, including umbilical cord blood stem cells have revived interest in optimizing cryopreservation techniques for cells and tissues (D. Krause, 2002). In particular, for stem cells and other cell types which are obtained in low numbers from donors, high recovery of these cell types is crucial. High recovery is also important in cryopreservation of engineered cells due to the high cost and length of time for manufacturing such cells. Emerging higher standards for cell and tissue banking (Guide to safety and quality assurance for organs, tissues and cells, $2^{nd}$ edition, 2004, Council of Europe Publishing, France), specifically stem cell banking, will be required to meet future needs of cell banking and therefore, optimal cryopreservation techniques are fundamental.

Currently, cryopreservation of cells has been most successful with the use of cryoprotectants and cryopreservation of stem cells has been most successful with the use of the permeating cryoprotectant, dimethyl sulfoxide (DMSO). There are, however, limitations to the use of DMSO. Adverse affects have been associated with infusion of stem cells preserved with DMSO (Davis et al., 1990; Egorin et al., 2001; Santos et al., 2003; Zambelli et al., 1998). Some researchers have attempted to reduce the amount of DMSO (Abrahamsen et al., 2002; Beaujean et al., 1998) or combine it with a non-permeating cryoprotectant, such as Hydroxyethyl starch (HES) (Donaldson, 1996; Halle et al., 2001; Katayama et al., 1997).

In non-clinical studies to examine the effects of low temperatures on cells, some cells have been cryopreserved without the use of a specific cryoprotectant such as DMSO (Farrant et al, 1974; Knight, Farrant et al. 1977). However, cooling profiles were not optimized and cell recoveries were not as high as with cryoprotectants. These studies were used in research to understand the mechanisms of cryoinjury and cryoprotection.

In current cryopreservation procedures, cells are generally cooled at a constant rate which is optimized for the cell type and cryoprotectant. This protocol has typically been approached empirically by varying cooling rates and the nature and concentration of cryoprotectants. In addition to cooling at a constant rate, other techniques have been described to examine the effects of low temperatures on cells, including a two-step freezing technique. The two-step freezing technique (J. Farrant et al., 1974) is a method to examine the effects of osmotic interactions on cell recovery over a broad range of subzero temperatures. In this procedure, lymphocytes were cooled rapidly to various subzero temperatures and held for various periods of time before being 1) thawed directly from that holding temperature or 2) rapidly cooled to −196° C. before thawing. McGann and Farrant later reported that the subzero temperature and the length of hold time at that temperature were factors to consider when attempting to maximize cell survival (McGann and Farrant, 1976). To date an easy method that can optimize cooling profiles for a cell type or for various cell types for cryopreservation of cells is not available and a reliable method that does not use cryoprotectants, especially permeating cryoprotectants, has not been recommended, especially for clinical use of the cells.

There is significant interest in designing an optimized cryopreservation protocol for all cell types and tissues, which maintains cell and tissue viability but does not require toxic cryoprotectants. Further there is a need for protocols to cryopreserve larger volumes of cells and tissues. Further there is a need to develop a model or optimization protocol to optimize cooling profiles to cryopreserve cells.

SUMMARY OF INVENTION

This invention relates to any non-linear cooling cryopreservation method for cryopreserving cells and/or tissue that is comprised of determining an optimal cooling profile for maximum recovery of specific cells and tissues, and applying the cooling profile to the respective cells and tissues. By non-linear cooling cryopreservation method we mean throughout any cryopreservation protocol for which, by design, temperature versus time is other than a single straight line or a profile made of two line segments with different slopes. In one embodiment, a non-linear cooling cryopreservation method is achieved by a non-constant cooling rate during at least a portion of the method. In another embodiment the non-linear cryopreservation method is achieved by a two-step cooling process, wherein the cells or tissue are cooled at a constant or non-constant rate to a first holding temperature (referred to throughout as hold temperature) and then subsequently at a constant or non-constant rate to a second temperature (referred to throughout as storage temperature).

The invention also relates to methods of optimizing cryopreservation methods by determining an optimal non-linear cooling profile and applying the profile to cryopreservation methods. The invention also relates to cryopreservation methods optimized by the method of the invention. This invention also relates to any product prepared for transplantation or other uses using such a protocol.

The optimal cooling profile is based in part or in whole on profiles determined using a computer simulation of cellular or tissue response during cooling and/or warming. The cellular responses are predicted from mathematical models using cellular osmotic transport properties, phase diagrams, and composition and thermodynamic parameters for the intra- and extra-cellular solutions for a particular cell type.

In one embodiment applicable to any cell type or tissue profiles are determined by requiring the amount of intracellular supercooling to remain below a maximum value throughout the method determined by correlating simulation predictions with viability outcomes. Supercooling is the amount the temperature is below the thermodynamic equilibrium freezing point of the solution. For instance, in one embodiment, the maximum intracellular supercooling is $10°$ C., i.e the cells or tissues are cooled without intracellular freezing or intracellular ice nucleation to a temperature below the freezing point of the intracellular solution but by not more than $10°$ C.

In one embodiment of the invention, the method of cryopreserving stem cells comprises cooling the cells or tissue at a constant or non-constant rate to a first temperature (hold temperature), holding at that temperature for a first period of time (the hold time), then cooling the cells or tissue at a constant or non-constant rate to a second temperature (storage temperature) for storing the cells or tissue. In one embodiment the hold time is between 1 to 30 minutes. In another embodiment the hold time is between 1 to 10 minutes. In another embodiment it is between 1 to 5 minutes. In yet another embodiment the hold time is between 1 to 3 minutes.

The cryopreservation methods of the invention can be used with cells stored without cryoprotectants. The protocols can also be used with cells stored with cryoprotectants, including permeating and non-permeating cryoprotectants. Such permeating cryoprotectants include but are not necessarily limited to DMSO, glycerol, propylene glycol and ethylene glycol. Such non-permeating cryoprotectants include but are not limited to sugars, starches, protein, serum, plasma or other macromolecules.

The invention can be applied to any types of cells, including but not limited to stem cells, other progenitor cells, red and white blood cells, sperm cells, oocytes, ova, cells for research or transplant purposes, and cellular materials derived from tissues and organs (including but not limited to pancreatic islet cells, chondrocytes, cells of neural origin, cells of hepatic origin, cells of opthalmolic origin, cells of orthopedic origin, cells from connective tissues, cells of reproductive origin, and cells of cardiac origin). Throughout this application, cells include cells organized as tissues. Stem cells include but are not limited to human peripheral blood stem cells, human umbilical cord blood stem cells and stem cells derived from tissues and solid organs or other sources, including but not limited to fetal and/or embryonic sources. The invention is not limited to human cell types and is extendable to all mammalian and non-mammalian species.

In one embodiment, the method of the invention can be used to cryopreserve stem cells, including but not limited to hematopoietic stem cells, umbilical cord blood stem cells, mesenchymal stem cells, stem cells derived from organs or tissues, and stem cells grown in culture (eg. TF-1 cells). As such, in one embodiment, the invention provides a stepped method of cryopreserving stem cells that comprises cooling the cells to a first temperature (hold temperature), holding at that first temperature for a first period of time, then cooling the cells to a second temperature for storing the cells.

In one embodiment of the invention, the amount of supercooling and concentration of intracellular KCl were used as predictors of cryoinjury.

Another embodiment of the invention includes any unit/equipment used to execute the non-linear cryopreservation protocols on cells in small or large samples or tissues. Including but not limited to a bulk freezing unit or a cryomicroscopy apparatus.

In one embodiment, the stem cells are cooled to a temperature between $-3°$ C. and $-30°$ C. held for 1 to 30 minutes, then cooled to a temperature below $-60°$ C. to store the cells. In one embodiment, the first temperature is between $-5°$ C. and $-15°$ C. The hold time is between 1 to 3 minutes and the second temperature is below $-60°$ C. including but not limited to liquid Nitrogen temperatures.

In another embodiment, the invention provides a method of restoring cryopreserved cells comprising warming the cells cryopreserved using a method of the invention noted herein using known protocols in the art, including but not limited to warming rates greater than $25°$ C./min, warming in a temperature regulated bath at a preset temperature ($0-40°$ C.), and warming at a constant rate greater than $25°$ C./min. In one embodiment the recovery of cells preserved by the methods of the present invention without cryoprotectants are comparable with that obtained using cryoprotectants. In one embodiment the recovery rate is 75% with non-permeating cryoprotectants.

In one embodiment of the invention, the cryopreservation methods of the invention and the cells and/or tissues recovered from cryopreservation using the methods of the invention can be used for research, transplantation, diagnostics and genetic testing, cell/tissue banking for surveillance, toxicity testing and for in vitro fertilization.

Other features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from reading the detailed description.

DETAILED DESCRIPTION OF THE INVENTION

Definitions

Figure 1:
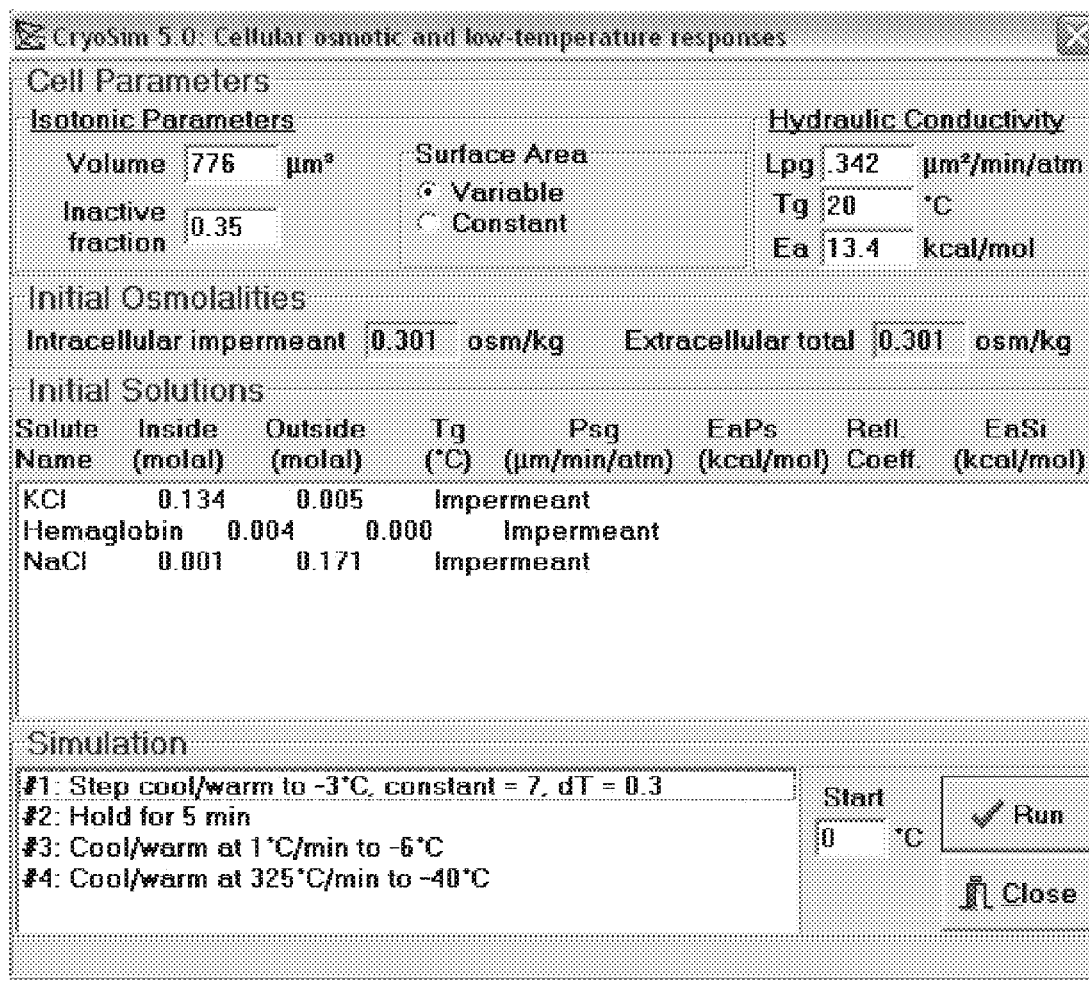
FIG. 1. Schematic of CryoSim5 program used to simulate cellular responses.

"Supercooling" is the amount the temperature is below the thermodynamic equilibrium freezing point of the solution. For instance, in one embodiment, the maximum intracellular supercooling is 10° C., i.e the cells or tissues are cooled without intracellular freezing or intracellular ice nucleation, under conditions where the difference between the temperature of the sample and the freezing point of the intracellular solution never exceeds 10° C.

"Cooling profile" or "temperature profile" is the specification of temperature as a function of time during the cryopreservation process. The mathematical derivative of this profile yields cooling rates at all time points during the protocol and therefore specification of cooling rates and duration of cooling can be determined from the cooling profile, conversely, cooling rates and duration of cooling can be specified to obtain a cooling profile over a particular time and temperature.

"Optimal cooling profile" is the cooling profile for maximum recovery of the cells and applying the cooling profile to the cells. The optimal cooling profile is determined in part or in whole using a simulation of cellular responses to cooling parameters. The cooling parameters comprise cell temperature, duration of temperature exposure, temperature as a function of time, and nature and concentration of cryoprotectants. The cellular responses are determined from mathematical models of osmotic transport properties, phase diagrams, and composition and thermodynamic parameters for the intra- and extra-cellular solutions for a particular cell type.

"Permeating Cryoprotectants" are cryoprotectants that can penetrate the cell membrane and be present intracellularly. Examples of permeating cryoprotectants include DMSO, glycerol, propylene glycol and ethylene glycol. These cryoprotectants tend to work by depressing the freezing point which lowers the temperature at which ice is formed, and by reducing the amount of ice formed which, in turn, lowers the temperature at which a specific concentration of electrolytes occurs.

"Non-Permeating Cryoprotectants" are cryoprotectants that do not penetrate the cell membrane and remain in the extracellular solution. Examples of non-permeating cryoprotectants include high molecular weight additives, such as sugars, starches, protein, serum, plasma and other macromolecules. These cryoprotectants tend to work by promoting osmotic water loss from cells at higher subzero temperatures but contribute to osmotic stresses on the cell.

"Cells" as used herein also includes cells organized into tissues.

"Non-linear Cooling". In the context of the cryopreservation method of the invention, Non-linear Cooling is meant that throughout any cryopreservation protocol for which, by design, temperature versus time is other than a single straight line or a profile made of two line segments with different slopes. In one embodiment, a non-linear cooling cryopreservation method is achieved by a non-constant cooling rate during at least a portion of the method. In another embodiment the non-linear cryopreservation method is achieved by a two-step cooling process, wherein the cells or tissue are cooled at a constant or non-constant rate to a first holding temperature (referred to throughout as hold temperature) and then subsequently at a constant or non-constant rate to a second temperature (referred to throughout as storage temperature).

"Two-Step Cooling" is a non-linear cooling method, wherein the sample is cooled to a first hold temperature and maintained at that temperature for a hold time before the sample is cooled to a second storage temperature.

"Hold Time" is the time at which the sample is maintained at the first hold temperature in the two-step cooling method.

"Hold Temperature" or "first temperature" in the two-step cooling method is the temperature at which or the temperature range within which the sample is maintained for the duration of the hold time.

"Storage Temperature" is the temperature at which the cells are stored. It can also be referred to as the "second temperature" in the two-step-cooling process. In one embodiment the storage temperature is below −60° C. In another, the sample is stored in liquid nitrogen. or anywhere in between these values.

Description

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

This invention relates to any non-linear cooling cryopreservation protocol for cryopreserving cells comprising of determining an optimal cooling profile for maximum recovery of the cells and applying the cooling profile to the cells. The optimal cooling profile is determined in part or in whole using a simulation of cellular responses to cooling parameters. The cooling parameters comprise cell temperature, duration of temperature exposure, temperature profile, and nature and concentration of cryoprotectants. The cellular responses are determined from mathematical models of osmotic transport, phase diagrams, and composition and thermodynamic parameters for the intra- and extra-cellular solutions for a particular cell type.

The cryopreservation protocol can be used with cells stored without cryoprotectants. The protocol can also be used with cells stored with cryoprotectants, including permeating and non-permeating cryoprotectants. Such permeating cryoprotectants include but are not limited to DMSO, glycerol, propylene glycol and ethylene glycol. Such non-permeating cryoprotectants include but are not limited to sugars, starches, serum, protein, serum, plasma or other macromolecules.

The invention can be applied to any types of cells, including but not limited to stem cells, other progenitor cells, red and white blood cells, sperm cells, oocytes, ova, cells for research or transplant purposes, and cellular materials derived from tissues and organs (including but not limited to pancreatic islet cells, chondrocytes, cells of neural origin, cells of hepatic origin, cells of opthalmolic origin, cells of orthopedic origin, cells from connective tissues, cells of reproductive origin, and cells of cardiac origin). Throughout this application, cells include cells organized as tissues. Stem cells include but are not limited to human peripheral blood stem cells, human umbilical cord blood stem cells and stem cells derived from tissues and solid organs or other sources, including but not limited to fetal and/or embryonic sources. The invention is not limited to human cell types and is extendable to all mammalian and non-mammalian species. In one embodiment of the invention, the non-linear cooling cryopreservation protocol comprises cooling the cells to a first temperature for a first period of time, then cooling the cells to a storage temperature for a second period of time prior to thawing.

In another embodiment of the invention, the non-linear cooling cryopreservation protocol can be executed on cells using a bulk freezing unit or a cryomicroscopy apparatus or other suitable apparatus, including one with a programmable thermocycler, that can be programmed to cool cells according to a particular cooling profile, for instance to maintain intracellular supercooling below a maximum amount or at a constant amount, or a profile that applies the optimized two-step cooling protocol.

The invention also relates to methods of optimizing cryopreservation protocols by determining an optimal non-linear cooling profile and applying the profile to cryopreservation protocols. The invention also relates to cryopreservation protocols optimized by the method of the invention.

The invention also relates to non-linear cooling cryopreservation protocols for cryopreserving stem cells.

In a specific embodiment of the invention, the method of cryopreserving stem cells comprises cooling the stem cells to a first temperature for a first period of time, then cooling the cells to a second temperature for storing the stem cells. In one embodiment, the stem cells are cooled to a temperature between −3° C. and −30° C. held at that temperature for 1 to 30 minutes, then cooled to a temperature below −60° C. to store the cells.

Description of Simulation Tool

The present invention provides a method and simulation tool that can be used to obtain cooling profiles and protocols for cryopreserving cells. The method can be used to obtain cooling profiles for cryopreserving cells that does not necessitate the use of cryoprotectants. Instead of using cryoprotectants to alter the properties of solutions so that cells may be cooled at a constant rate (normally 1° C./min) and achieve high recovery, in one aspect of the invention, the inventors' approach (Ross-Rodriguez, 2003(a); Ross-Rodriguez et al., 2003(b)) has been to use the properties of the intracellular and extracellular solutions and osmotic transport parameters of subject cells to design optimal cryopreservation protocols. A novel aspect of this approach is that the temperature profile is not constrained to be linear. Rather, the intracellular and extracellular solution properties, along with cellular osmotic properties, are used to generate a temperature profile that minimizes cryoinjury.

During the course of the inventors' research on cryoinjury and cryoprotection, the inventors have developed a mathematical model of cellular osmotic responses at low temperatures using real (nondilute) solution assumptions for both the carrier solution and the cellular cytoplasm (McGann and Elliott, 2003). In one embodiment of the invention, this model has been implemented in a computer program as a simulation tool to calculate intracellular and extracellular parameters as the temperature changes and ice forms or melts. The simulation tool can be used to generate an optimized temperature profile for cooling the cells in order to obtain maximal recovery of the cells upon thawing. The tool can be applied to any cell type by using appropriate parameters of the cells and solutions.

In some embodiments of the invention, simulations are based on changes in the composition of the extracellular solution as water is converted to ice during cooling, and the osmotic responses of cells to these changes.

Features of the simulation include the use of the phase diagram information for the extracellular and intracellular solutions, the osmotic characteristics of the plasma membrane and the temperature dependencies of the cellular osmotic parameters to calculate the cellular osmotic responses to the concentration of solutes in the residual liquid in the presence of ice at low temperatures.

A computer program was developed (using the Delphi programming language) to perform the simulations based on either calculated or measured temperature profiles. The program also includes a function to generate the temperature profile required to maintain the cytoplasm at a constant degree of supercooling. One embodiment of the present invention, is to experimentally determine the maximum tolerable amount of intracellular supercooling, to use this amount of supercooling in simulations to generate non-linear temperature profiles for cryopreservation. In addition to the resulting temperature profile, all calculated parameters are reported as a function of time to allow access to both intracellular and extracellular concentrations and fluxes.

Predictors of Cryoinjury

One embodiment of this invention uses the amount of maximum intracellular supercooling as a predictor of cryoinjury related to intracellular ice formation, and the maximum intracellular KCl concentration as a predictor for cryoinjury related to exposure to concentrated solutions.

Application of Method to Different Cell Types and Tissues

The invention can be applied to any types of cells, including but not limited to stem cells, other progenitor cells, red and white blood cells, sperm cells, oocytes, ova, cells for research or transplant purposes, and cellular materials derived from tissues and organs (including but not limited to pancreatic islet cells, chondrocytes, cells of neural origin, cells of hepatic origin, cells of opthalmolic origin, cells of orthopedic origin, cells from connective tissues, and cells of reproductive origin, and cells of cardiac and cardiovascular origin). Stem cells include human peripheral blood stem cells, human umbilical cord blood stem cells, stem cells derived from tissues and solid organs or other sources, including fetal and/or embryonic sources, as well as mixtures of stem cells with other cells and from different sources. Tissues include cornea, cartilage, bone, skin, heart valves, Islets of Langerhans, embryos from humans, animals, fish, shellfish and plants, and ovarian tissues from humans and animals. The invention is not limited to human cell types and is extendable to all mammalian and non-mammalian species.

Applications of this invention to different cell types utilize information on various cell parameters, including the osmotic transport parameters and their temperature dependencies, solution properties of the cytoplasm, solution properties of the extracellular solution and any cryoprotectant or other solutes present and the relationship between intracellular supercooling and intracellular freezing of different cell types. Some of these properties will not change significantly between different cells. Solution properties, for example, depend primarily on the concentrations of electrolytes and proteins, which are similar for various types of cells. Similarly, the incidence of intracellular freezing as a function of supercooling is likely to be similar for different types of cells since there are likely similar mechanisms of ice nucleation in cells, whether ice is initiated by spontaneous nucleation in the cells, through aqueous pores in the plasma membrane (Acker et al., 2001), by surface-catalyzed nucleation (Toner, 1993), or by osmotic rupture of the plasma membrane (Muldew and McGann, 1941). Conversely, the osmotic transport parameters and their activation energies depend strongly on cell type and stage of differentiation (McGrath, 1988).

Obtaining Cellular Osmotic Properties

Cellular osmotic properties can be obtained from the literature (see for example Gao et al., 1998 and Hunt et al., 2003). For cell types whose osmotic properties have not yet been published, the osmotic properties can be measured as described by the inventors in the examples and in the literature (Ross-Rodriguez, 2003(a)).

Measuring Solution Properties

Calculations of osmotic transport at low temperatures require descriptions of the intracellular and extracellular solutions. Phase diagrams of binary and other solutions show that solution behavior over the range of temperature between freezing and −60° C. is nonlinear, so an assumption of dilute solutions is inappropriate. The constants in any equations that describe non-dilute behavior are therefore required for the major intracellular and extracellular solutes. This information has been gathered for particular cell types from the literature. Intracellular and extracellular solute information for cell types can be gathered empirically, from the literature, and from the inventors' own previous work. (MacMillan and Mayer 1945, Freedman and Hoffman 1979, Elliott et al., 2002).

Monitoring Cryoinjury

Several in vitro methods can be applied to assess stem cell recovery after experimental treatment and to further optimize hold temperatures and hold times. These assessments may include but are not limited to membrane integrity, metabolic and other functional assays and/or colony growth in culture, and fluorescent assays, such as SYTO/EB as noted in the examples below.

Infusible Extracellular Compounds

The inventors demonstrate that temperature profiles can be generated to avoid intracellular freezing and to reduce cryoinjury related to exposure to high concentrations of solutes, similar to results for human lymphocytes (Farrant et al., 1.974). However, to simultaneously meet these criteria for some cells, i.e. conditions required to avoid intracellular freezing may already subject the cells to lethal exposure to the solution it may be optimal to use infusible extracellular compounds. In this case further embodiments of the invention include use of infusible extracellular compounds, including but not limited to sugars, starches, such as Pentastarch and hydroxyl starch, serum, proteins or plasma as cryoprotectants.

Cryopreservation Protocol for Stem Cells

A two-step freezing protocol used by Farrant et al. to obtain high recovery of human lymphocytes cryopreserved in serum alone (Farrant et al., 1974) was optimized using simulation of a stem cell line (TF-1 cells, a hematopoietic stem cell line) without cryoprotectant (Ross-Rodriguez, 2003) and further optimized, and validated using experimental measurements of post-thaw cell recovery. Osmotic transport parameters were measured for the TF-1 cells and used in simulations of the two-step cooling protocol. The maximum degree of intracellular supercooling over the course of the cooling protocol was used as a predictor of cryoinjury due to intracellular freezing, and the maximum intracellular potassium chloride concentration used as a predictor of cryoinjury due to exposure to the concentrated solutes. Minimum values for the predictors of cryoinjury from the simulation indicated the range of hold temperatures and hold times where cell recovery was expected to be maximal in the absence of cryoprotectants.

Experimental measurement of TF-1 cell recovery using membrane integrity showed maximal recovery in the hold temperature range predicted by the simulations and low recovery at hold temperatures outside the predicted range. The maximum recovery of TF-1 cells without cryoprotectant thawed from −196° C. was equivalent to the recovery after conventional cryopreservation (cooling at 1° C./min in the presence of 10% DMSO). In a specific embodiment, the zone of hold temperatures (−3° C. to −30° C.), when held for 1-30 minutes, confer comparable protection against injury to the standard 10% DMSO solution using conventional cooling profiles.

Results of these experiments supported the concept of using theoretical predictors of cryoinjury in the use of simulations to reduce empirical experimentation in optimization of cryopreservation protocols. These results also demonstrate the value of simulations to be used in protocol design.

EXAMPLES

The following examples are intended to illustrate various embodiments of the invention and are intended to be interpreted in a non-limiting sense.

This invention relates to the cryopreservation of cells. More particularly it relates to non-linear cooling methods for the cryopreservation of cells. In another embodiment, the invention relates to non-linear cooling methods for the cryopreservation of cells that do not require the use of cryoprotectants for cell recovery optimization, more particular permeating cryoprotectants such as DMSO, glycerol, propylene glycol and ethylene glycol that can have toxic, damaging osmotic, harmful or other undesired effects on recovered cells especially cells for clinical use.

In yet another embodiment the invention relates to the optimization of non linear cooling cryopreservation of cells by taking into account:
  (a) the effects of intracellular freezing on cell viability; and
  (b) solution effects on cell viability; and
  (c) dependence of the above factors on time and temperature
  (d) osmotic parameters for the extracellular solution and for the intracellular solution for a particular cell type.

In one embodiment, the invention provides a method to optimize cooling profiles for cryoprotecting cells comprising:
  (a) determining the osmotic parameters of the cell type, including osmotically-inactive fraction, hydraulic conductivity and its Arrhenius activation energy;
  (b) determining the thermodynamic phase diagram of the intracellular and extracellular solutions
  (c) determining the amount of intracellular supercooling that leads to intracellular freezing (e.g. maximum supercooling);
  (d) using the osmotic parameters of the cell type (a), the thermodynamic phase diagram of the intracellular and extracellular solutions (b), and maximum supercooling amounts (c) under various conditions to model the cellular response to low temperatures based on preferred selected criteria, eg. setting the maximum amount of (i) intracellular supercooling to a desired level, for instance does not exceed 10° C. (for 2 step or constant supercooling profiles) and/or (ii) intracellular concentration of KCl to a desired level, for instance does not exceed 3M;
  (e) optionally empirically testing the simulations experimentally to compare with theoretical data; and
  (f) optionally repeating steps (a) to (e) to adjust for instance constants and values of osmotic and thermodynamic properties of the cells and to further optimize the cooling profile.

In order to make a simulation of a cooling cryopreservation profile, in one embodiment, internal and external solution compositions, as well as the values of cellular osmotic properties (e.g. $L_p$, $E_A$ of $L_p$, $V_{iso}$, $V_b$, $\pi_{iso}$, $\pi_i$, $\pi_e$ are used. These properties can be obtained from the literature (see for example Gao et al., 1998 and Hunt et al., 2003) or by experimentation. For cell types whose osmotic properties have not yet been published, the osmotic properties can be measured as described by the inventors in the examples and in the literature (Ross-Rodriguez, 2003(a)). As well, the thermodynamic solution properties (K1, $B2_i$, B3) can also be obtained from the literature, from experimentation or from existing experimental data (Bannerman, Elliott et al. 2005).

In one embodiment, the invention relates to a method of optimizing cooling profiles for cells by obtaining, e.g. through experimentation or prior literature, the values of one or more or all of the following:
  (a) $L_p$=hydraulic conductivity
  (b) $E_A$=activation energy of $L_p$
  (c) $V_{iso}$=isotonic volume
  (d) $V_b$=osmotically inactive fraction
  (e) $\pi_{iso}$=isotonic osmolality
  (f) $\pi_i$=intracellular osmolality
  (g) $\pi_e$=extracellular osmolality;
  (h) $B2_i$, $B3_i$=the second and third, respectively, osmotic virial coefficients for each solute, i,
and inserting the values into thermodynamic equations, such as the following coupled equations and obtaining a mathematical solution that can be used for cooling profile simulations for various solution parameters or cell types.

A range of equations can be used in particular simulations. A person skilled in the art would appreciate that a variety of equations may be used to obtain the desired osmotic and thermodynamic properties noted above and represented in the equations below. This invention is intended to encompass any and all such equivalents.

In one embodiment, the equations include one or more of the following:

1. The Jacobs and Steward model (Jacobs and Steward 1932)

$$\frac{dV}{dt} = L_p \cdot A \cdot R \cdot T(\pi_i - \pi_e)$$

where V is the water volume in the cell ($\mu m^3$), t is the time (min), $L_p$ is the hydraulic conductivity or rate at which water moves across the cell membrane; A is the cell surface area ($\mu m^2$), R is the universal gas constant (kcal/mol/K), T is the absolute temperature (K), $\pi_e$ is the extracellular osmolality (osmoles/kg water) and $\pi_i$ is the intracellular osmolality (osmoles/kg water). $L_p$ can be determined using measurements of the kinetics of volume change over time when exposed to anisotonic solutions. This equation provides a function of a change in volume over time in light of cell membrane characteristics (e.g. hydraulic conductivity) for a particular cell type and osmality of the internal and external solutions. A suitable replacement membrane transport model could also be used instead of this equation.

2. The Boyle van't Hoff relationship (Lucke and McCutcheon 1932)

$$\frac{V_{eq}}{V_{iso}} = \frac{\pi_o}{\pi}(1 - v_b) + v_b$$

where $V_{eq}$ is the equilibrium volume ($\mu m^3$) of the cell, $V_{iso}$ is the isotonic volume ($\mu m^3$), $\pi_o$ is the isotonic osmolality (osmoles), $\pi$ is the experimental osmolality (osmoles), and $v_b$ is the osmotically-inactive fraction. Through graphical analysis of $V_{eq}/V_{iso}$ as a function of $\pi_o/\pi$, $v_b$ can be determined by extrapolating the line by linear regression to the y-intercept. This equation is used to calculate the osmotically-inactive fraction, that fraction of the cell volume that is not involved in the osmotic activities of the cell, by expressing the equilibrium cell volume after exposure to anisotonic solutions of impermeant solutes. A person skilled in the art would appreciate that a replacement equilibrium equation could also be used.

3. The Arrhenius temperature dependence of Lp (Voet and Voet 1995)

$$L_p = L_p^o \cdot \exp\left(\frac{-E_a}{R \cdot T}\right)$$

where $L_p^o$ is a fitting constant, R is the universal gas constant (kcal/mol/K) and T is the absolute temperature (K). $E_A$ is the Arrhenius activation energy of $L_p$ and is used to describe the temperature dependence of $L_p$. A person skilled in the art would appreciate that replacement temperature dependence for the hydraulic conductivity could also be used.

4. A specified Temperature as a function of time, i.e. T=F(t) such as prescribed cooling rates at different times or with a function or functions including but not limited to either an experimentally determined numerical function or for certain portions an analytical equation such as Newton's Law of Cooling: (Incopera and Dewitt 2002)

$$\frac{dT}{dt} = k \cdot \Delta T$$

where dT/dt is the rate of change in temperature change in the sample with time, k ($s^{-1}$) is the fitting constant obtained from experimental data (Ross-Rodriguez 2003), and $\Delta T$ is the difference in temperature between the bath and the sample. A person skilled in the art would appreciate that a replacement cooling profile could also be used. Alternatively the cooling profile can be left as an adjustable function obtained as an output of a simulation.

5a. The Bannerman-Elmoazzen-Elliott-McGann equation (Elliott et al., 2002; Bannerman et al., submitted, 2005).

$$\pi = \sum_{i=1 \ldots n} \left[ m_i + B2_i \cdot m_i^2 + B3_i \cdot m_i^3 + \sum_{j=i+1 \ldots n} [(B2_i + B2_j) \cdot m_i \cdot m_j] \right]$$

where $\pi$ is osmolality of the solution, m is the molality of the solute, and B2 and B3 are fitting constants for specific solutes in water. For electrolytes, the molality is multiplied by an empirically determined "dissociation" constant. The constant B3 is non-zero only for solutes with highly nonlinear behaviour, such as macromolecules. A replacement description of the solution phase diagrams, ie. freezing point as a function of solution composition and osmolality as a function of composition, could also be used.

5b. The freezing point of the intracellular or extracellular solution, $T_{FP}$, can be described by the equation (Elliott et al., 2002))

$$T_{FP} = K\pi$$

where K is the molal freezing point depression constant for water, and $\pi$ is the osmolality of the solution, 6. The amount of intracellular supercooling (S) at each instant is then given by $$S = T - T_{FP}.$$

With temperature as a function of time (such as equation 4) as an input, Equations 1, 2, 3, 5, 6 form a coupled set of differential equations that can be solved, for instance, by a computer yielding cell volume, molality of each impermeant intracellular component, freezing point of the intracellular solution and amount of supercooling each as a function of time during the cooling profile. Since the cooling profile is specified, there is a one-to-one correspondence of temperature and time so that one also has then cell volume, molality of each impermeant intracellular component, freezing point of the intracellular solution and amount of supercooling each as a function of time during the cooling profile.

Figure 13:
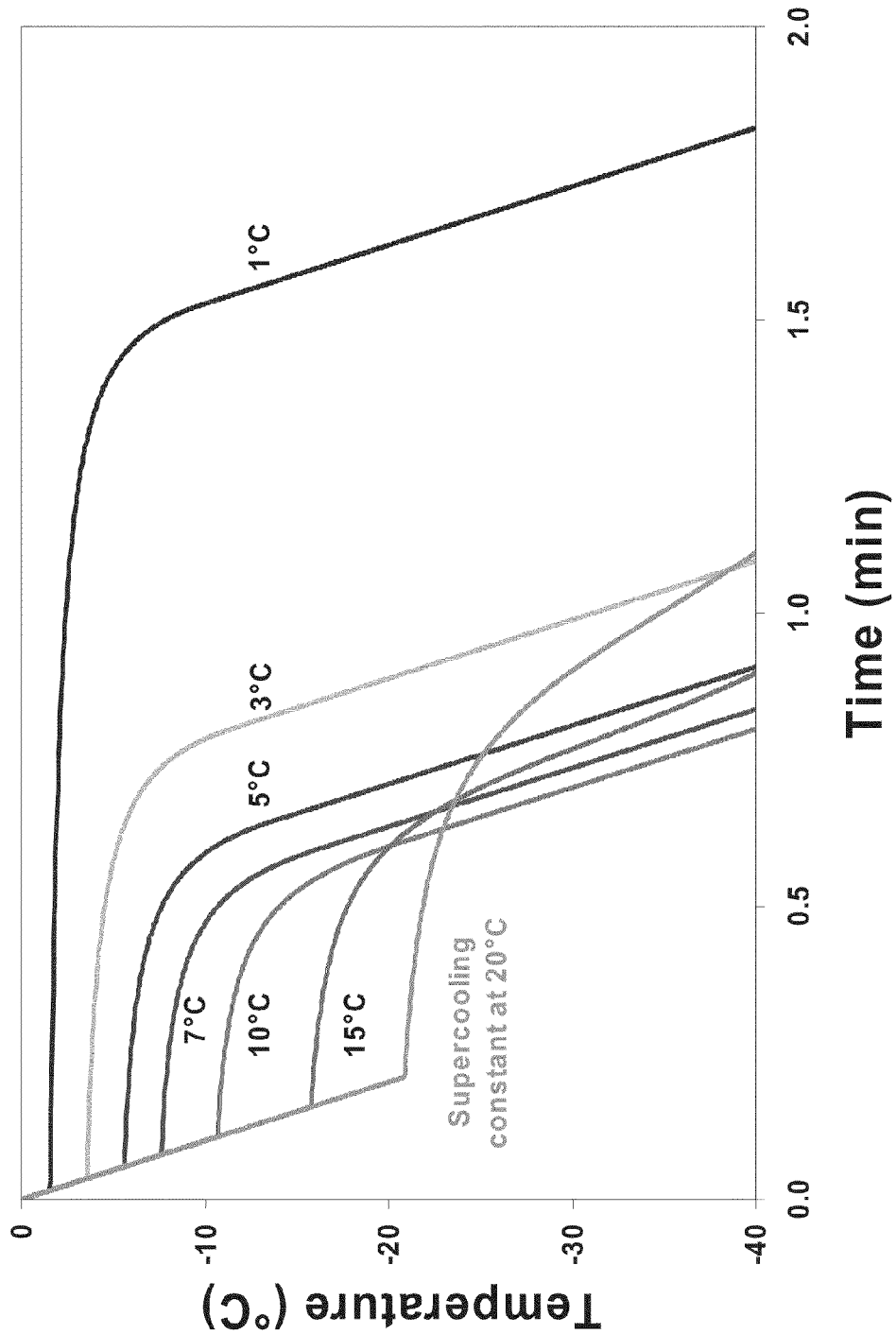
FIG. 13 Optimal non-linear cooling profiles calculated for TF-1 cells using specified maximum amount of supercooling. The calculated profile is that which would maintain the intracellular supercooling at or below the specified amount as TF-1 cells are cooled. In the embodiment shown here a maximum cooling rate has been imposed until the cells first reach the specified amount of intracellular supercooling.

In an alternative embodiment, the cooling profile can be left unspecified, for instance by omitting equation 4. and specifying the amount of supercooling, S, in equation 6. The coupled equations 1, 2, 3, 5, 6 can then be solved yielding temperature as a function of time as an output along with cell volume, molality of each intracellular component, freezing point of the intracellular solution, each as a function of time during the cooling profile. Applying such a temperature profile to the cells would keep the cells below a maximum amount of intracellular supercooling as the cooling proceeds. Example profile for TF-1 cells calculated to restrict intracellular supercooling to specified values are shown in FIG. 13. In one embodiment, a maximum practical cooling rate has been imposed until the cells first reach the specified amount of intracellular cooling.

In one embodiment, a person skilled in the art, to obtain a solution to the set of Equations would appreciate that in addition to known values of the parameters, (a)-(h), molar volumes of all components, a mass or mole balance and unit conversions as appropriate would be used to obtain the cooling profile. In one embodiment, the set of equations can be solved on a commercially available (or programmed by someone skilled in the art) differential and algebraic equation solving computer program.

The method of the invention can also be used to develop a cooling profile when there is a cryoprotectant, such as a permeating cryoprotectant. A similar set of equations can be used when there is a permeating solute (such as a permeating cryoprotectant like DMSO). In this case, the set of equations consists of 1-6 with an additional equation describing the permeant solute membrane mass transport.

For instance, the membrane mass transport equation for permeable solutes may be, for example [Jacobs, 1933; Jacobs et. al., 1932]

$$\frac{dN_s^i}{dt} = P_s A (m_s^e - m_s^i)$$

where $N_s^i$ is the number of moles of intracellular solute, Ps is the membrane permeability to that solute, $m_s^e$ and $m_s^i$ are respectively the extracellular and intracellular molality of the solute or a replacement equation, including but not limited to extensions of equation 7 to account for non-idealities of solutions (Elmoazzen, et. al., 2004); and/or Kedem-Katachlsky type reflection coefficient (Kedem et.al, 1958).

Again, either i) temperature profiles, such as described in equation 4, are given as an input and then 1, 2, 3, 5, 6 plus the additional permeant solute membrane mass transport equation, equation 7, are solved to determine the amount of supercooling as a function of time, (as well as cell volume, molality of each intracellular component, and freezing point of the intracellular solution and intracellular supercooling each as a function of time); and/or ii) the temperature profile is omitted and the amount of supercooling in equation 6 is set to a constant, maximum value, and then equation 1, 2, 3, 5, 6 plus the additional permeant solute membrane mass transport equation, equation 7, are solved yielding the optimal temperature as a function of time to be followed as the optimal cooling profile (as well as cell volume, molality of each intracellular component, and freezing point of the intracellular solution each as a function of time).

The result from this method is a cooling profile corresponding to prescribed conditions, or a set of cooling profiles corresponding to a set of prescribed conditions.

In one embodiment, experiments, following the specified temperature profiles are performed, the viability of the cells after the application of the protocol is assessed and the experimental results can be used To determine:

(i) what amount of supercooling if reached at anytime during the a cooling protocol is tolerable by a particular cell type without intracellular ice damage; and/or (ii) what amount of constant supercooling yields a temperature profile that is tolerable by the cells; and/or (iii) what concentration of intracellular solutes (such as KCl) if reached at anytime during the cooling profile (maximum KCl) is tolerable by the cells, and to further optimize the cooling profile and simulation by adjusting fitting constants and the like.

As an example of the one embodiment of the invention, for instance, for TF-1 cells in the sample calculations shown, the isotonic solution composition (a) and osmotic parameters (b), the cooling profiles and the solution thermodynamic parameters for TF-1 cells as listed in Table 1 can be inputted into the simulation protocol and coupled equations to determine an optimal cooling profile for a cell type, for instance at a preferred maximum supercooling amount and KCl concentration throughout the profile. The cooling profile would include rate of cooling over range of time, including any hold times and hold temperatures taking into account change of volume over time, change of temperature over time and other changes in osmotic or thermodynamic parameters over time.

In one embodiment, the method of the invention can be used to determine optimal cryopreservation solution parameters and to develop cryopreservation solutions. Such solutions can be optimized for particular cell types and tissues.

In one embodiment the invention provides a method for establishing cooling profiles of supercooling versus time and [KCl] versus time and selecting those protocols which meet a desired requirement on intracellular supercooling and intracellular [KCl] for example those parameters that provide for cooling profiles wherein the supercooling amount does not exceed 10° Celsius and intracellular KCl concentration does not exceed 3M or obvious chemical equivalents of these amounts, e.g. +/−10%. However a person skilled in the art can use the method and vary the maximum amounts of supercooling and KCl concentration depending on desired cell viability or cell recovery. In one embodiment the invention can provide cell recovery of 75% or more with the use of non-permeating cryoprotectants after thawing. In another embodiment, the invention can provide cell recovery without cryoprotectants that are comparable to those obtained with cryoprotectants, such as permeating and/or non-permeating cryoprotectants. The method of the invention also involves methods of non-linear cryopreserving cells and recovering cryopreserved cells. Known methods can be used to recover cells cryopreserved using the methods of the present invention, such as warming rates greater than 25° C./min, warming in a temperature regulated bath at a preset temperature (0-40° C.), and warming at a constant rate greater than 25° C.

In the method of the invention experimental parameters can be inserted into equations to obtain constants for various cell types and solution/condition parameters. Equations then can be used to develop simulated, or in one embodiment optimal, cooling profiles for different solutions for that particular cell type. In one embodiment, cooling profiles are selected that limit the maximum amount of supercooling (as an indicator of intracellular freezing), and KCl concentration (as an indicator of solute effects and cell viability) to optimal levels. In another embodiment, cell volume over a particular cooling profile can be used to select for desired cooling profiles, one that permits some equilibrium with extraceullar solution conditions and dehydration to limit the amount of water within the cells and minimize intracellular freezing, while preventing too much dehydration that would adversely effect cell viability.

In one embodiment, the amount of supercooling does not exceed 10° C. or obvious chemical equivalents thereof. In another embodiment, the optimal concentration of intracellular KCl does not exceed 3M or obvious chemical equivalents thereof. In one embodiment, the invention relates to any cooling profile which is based on restricting the amount of intracellular supercooling during cooling to below a specified amount, e.g. 10° C.; and/or the intracellular solute concentration to below a specified amount, e.g. 3M KCl. However, the maximum amount of intracellular supercooling tolerable by a certain cell type in a certain circumstance may vary, for example, between 1° C. and 40° C. and the maximum amount of intracellular solute concentration represented by [KCl]i, tolerable by a certain cell type in a certain circumstance may vary, for example, between 1M and 8M.

In one embodiment, the cells are cooled to a temperature between −3° C. and −30° C. held for 1 to 30 minutes, then cooled to a temperature below −60° C. to store the cells. In another embodiment, the cells are cooled to a temperature of between −5° C. and −15° C., for a hold time between 1 to 5, or in another embodiment 1 to 3 minutes and then cooled to a second or storage temperature below −60° C. including but not limited to liquid Nitrogen temperatures. Again, in one embodiment, it should be noted that the cells can be held at a constant temperature within the desired range throughout the desired hold time or at a non constant temperature within the range. In another embodiment, cells are cooled to the hold temperature in 0.1 to 5 minutes using linear or nonlinear profiles. In yet another embodiment, cells are cooled from the hold temperature to the second or storage temperature in 0.1 to 5 minutes using linear or nonlinear profiles The above variables can be adjusted with different solutions and the presence and absence of cryoprotectants, such as permeating, non-permeating or a mixture of permeating and non-permeating cryoprotectants. Examples of permeating cryoprotectants include but are not necessarily limited to DMSO, glycerol, propylene glycol and ethylene glycol. Examples of non-permeating cryoprotectants include but are not necessarily limited to sugars, starches, proteins, serum, plasma and other macromolecules.

In another embodiment, a two-step cooling profile is used, wherein cells are cooled to a first temperature (at either a constant or non-constant rate i.e. following a linear or non-linear temperature profile) and held for a desired period of time to enable equilibration with extracellular solutions, while minimizing intracellular freezing and solution effects and then cooling to a second temperature or storage temperature at a constant or non-constant rate (or following a linear or non-linear temperature profile), that enables high recovery of cells recovered from the storage temperature.

A person skilled in the art would appreciate that similar methods can be used to determine optimal cooling cryopreservation profiles for tissues.

Example 1

Theoretical Design of a Cryopreservation Protocol 1.1 Introduction

The cellular responses to the formation of ice in surrounding solution are largely dependent on the movement of water across the plasma membrane. Ice formation causes osmotic imbalance across the cell membrane forcing water out of the cell to maintain equilibrium with the extracellular solution.

The properties of the cell membrane, specifically the osmotic parameters, as well as the solution thermodynamics of the intracellular and extracellular solutions govern these changes in cell volume. The osmotic parameters can be used in simulations to theoretically model cellular responses to low temperatures. Simulations also provide precise results regarding changes in cell volume and the amount of supercooling. These results can then be used for comparisons between cryopreservation protocols and for comparison between different cell types which may be present in one tissue. Ultimately, simulations allow for unlimited theoretical protocols to be explored by controlling cooling and warming conditions, hold times, hold temperatures, and the components of the intracellular and extracellular compartments for any cell type for which the osmotic parameters are known (Ross-Rodriguez, 2003).

To distinguish between the two types of injury, solution effects and intracellular ice formation, the inventors simulated the empirical procedure of two-step freezing.

The objective of this example was to determine the theoretical responses of TF-1 cells, a model for hematopoietic stem cells (HSC) (Kitamura, 1989(a); Marone, 2002), to subzero hold temperatures and to hold times at those temperatures. Simulations were done using the osmotic parameters of TF-1 cells reported in Ross-Rodriguez, 2003. The objective of these simulations was to theoretically determine the conditions of TF-1 cells at various stages of a freezing protocol. Maximum levels of intracellular electrolyte concentrations ($[KCl]_i$) and of supercooling were examined upon cooling the cells with the two-step protocol as predictors for solution effects injury and intracellular ice formation injury, respectively.

1.2 Simulations of Two-Step Freezing Protocol

Methods

Simulations were performed according to those done in Ross-Rodriguez, 2003 using the osmotic parameters of TF-1 cells (Table 1) in the CryoSim5 program (Dr. Locksley McGann, University of Alberta, Canada). The simulations were based on a two-step freezing technique, which has been used to examine the effects of high solute concentrations and intracellular ice formation on cell survival during freezing (Farrant, 1977). The cryopreservation protocol was defined by assigning a starting temperature and then varying the cooling rates, based on typical two-step freezing procedures. Supercooling and $[KCl]_i$ were used as predictors of potential intracellular ice formation and solution effects, respectively. Coupled equations 1-6, noted above were used to obtain the simulations and the results noted below.

Temperature Profiles

Figure 2:
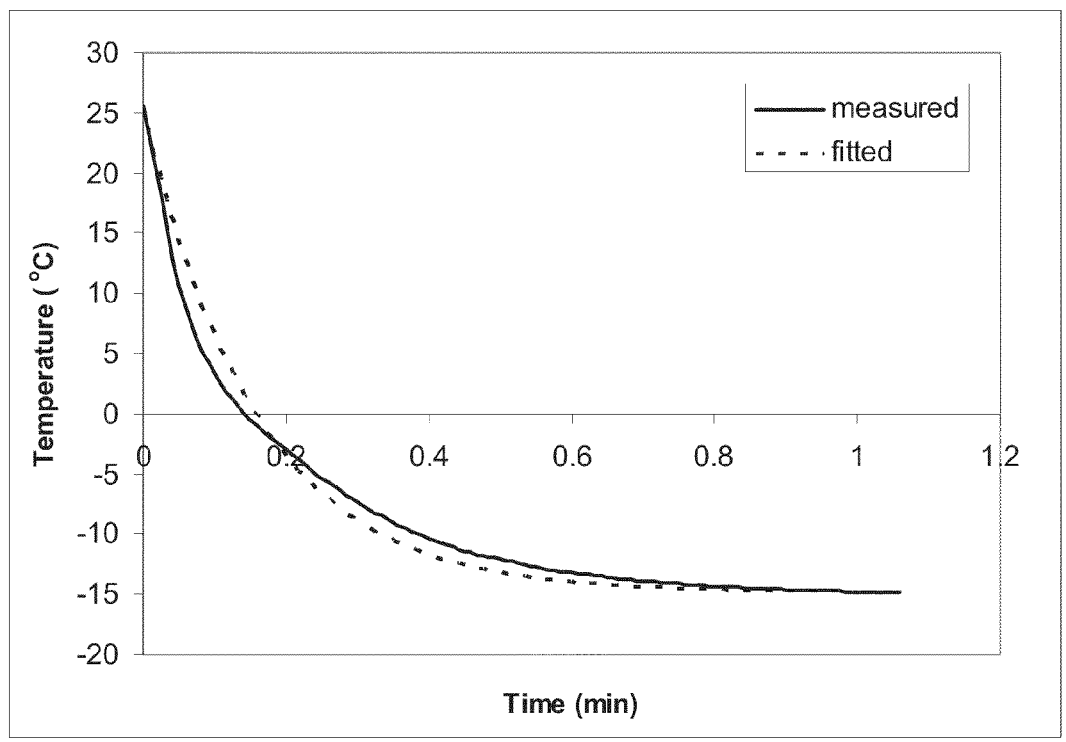
FIG. 2. A representative cooling profile for TF-1 cells in the stepped method, cooled from room temperature to $-15°$ C. measured with a thermocouple (measured). The curve is fitted according to Newton's Law of Cooling (fitted).

The two-step freezing technique involved rapidly cooling the samples to various subzero hold temperatures before either being thawed directly in a 37° C. water bath or cooled rapidly in liquid nitrogen first and then thawed (McGann, 1979). For the simulations, cells were cooled using a temperature profile derived from Newton's Law of Cooling. Newton's Law of Cooling describes the temperature change in response to heat transfer which depends on the difference in temperature between the bath and the sample. Alternatively, more sophisticated heat transfer modeling could be used if needed (Incropera & Devitt, 2002). A fitting constant in Newton's Law of Cooling was determined by monitoring the cooling profile of a sample taken from room temperature and exposed to the experimental subzero temperature with a Type T thermocouple (Omega, Laval, Canada). FIG. 2 is a representative cooling profile of a sample cooled from room temperature to −15° C. This profile was then fitted to a curve and the equation was then used in simulations. The variations between the experimental and fitted curves were due to the latent heat of fusion. Alternatively a numerical representation of the experimental curve could be used.

Simulations were performed in which cells with no cryoprotectant were cooled to various subzero hold temperatures ranging from −3° C. to the homogenous nucleation temperature of water, or in one embodiment to −40° C. and held at that temperature for 0.3, 0.5, 0.7, 1, 2, 3, 5, 7, or 10 minutes, prior to being cooled at 325° C./min to the storage temperature (Ebertz, 2002).

1.3 Results

Changes in Cell Volume During Cooling

Figure 3:
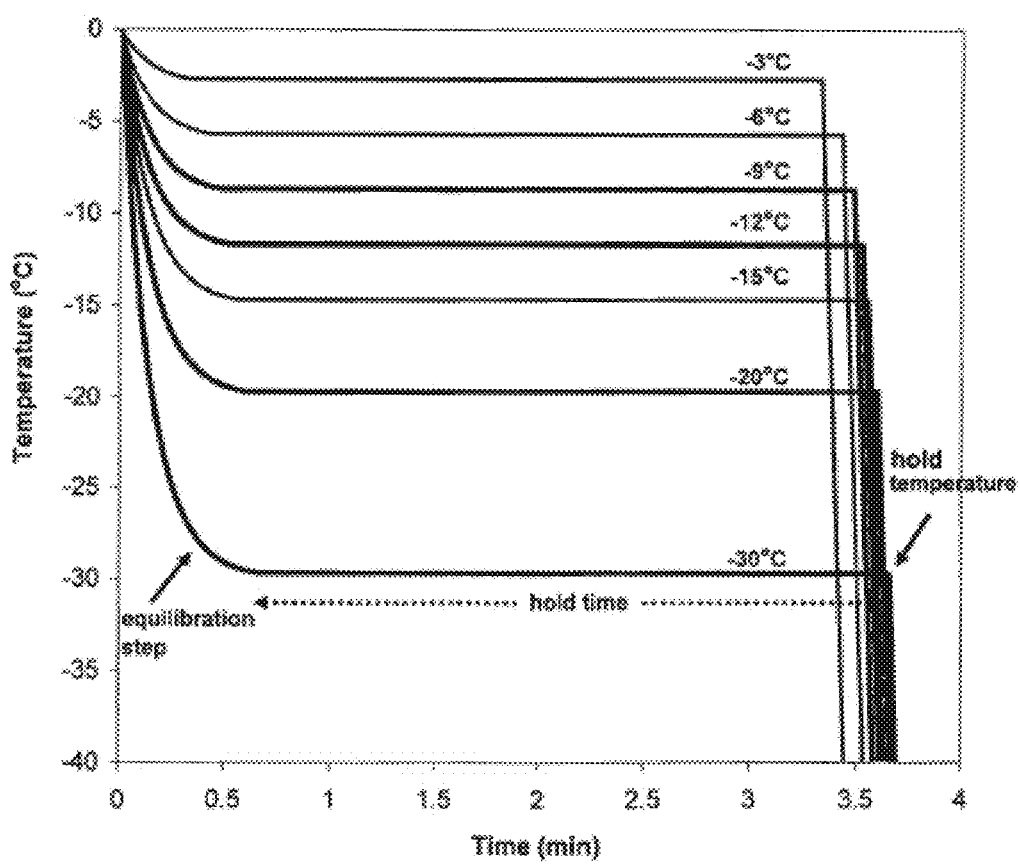
FIG. 3. Simulations of temperatures as a function of time for TF-1 cells in the stepped method, cooled to various subzero hold temperatures ($-3°$ C. to $-40°$ C.) using Newton's Law of Cooling (constant=$6.6$ s$^{-1}$) and held for 3 minutes, prior to rapid cooling at $325°$ C./min.
Figure 4:
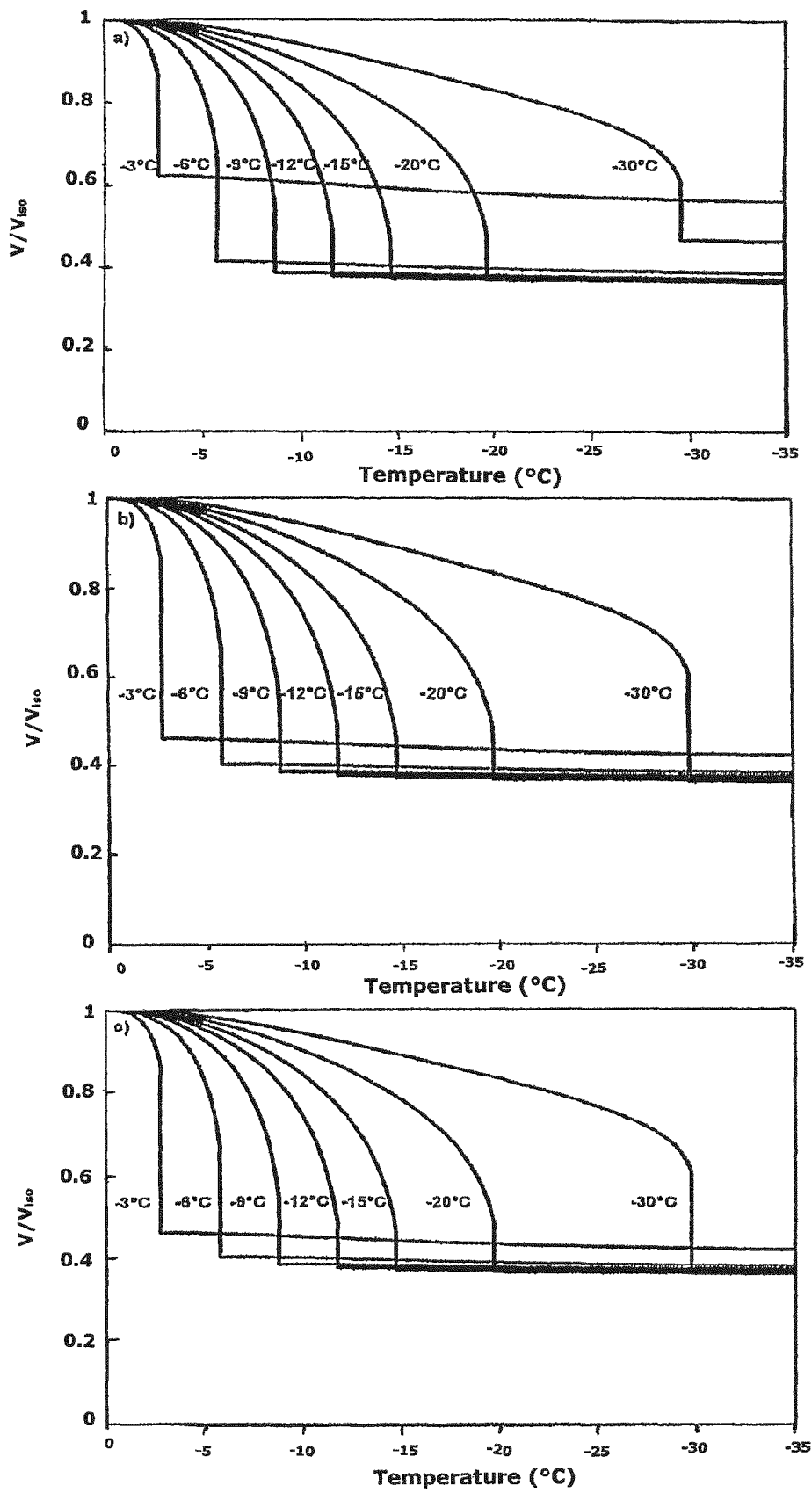
FIG. 4. Example simulations of volume as a function of temperature for TF-1 cells in the stepped method, cooled according to Newton's Law of Cooling (constant=$6.6$ s$^{-1}$) to various subzero hold temperatures ($-3°$ C. to $-40°$ C.) and held at that temperature for (a) 0.5 min., (b) 3 min., and (c) 10 min., prior to rapid cooling at $325°$ C./min.

FIG. 3 shows simulation results of temperature as a function of time for TF-1 cells cooled to various subzero hold temperatures ranging from −3° C. to −30° C., held for various hold times (minutes), prior to being cooled at 325° C./min to the storage temperature Based on the results from the simulations, the hold times were grouped according to similarities of changes in cell volume, $[KCl]_i$, and supercooling: Hold times of 1 minute or less will be represented by the 0.5 minute results; hold times between 2 and 5 minutes will be represented by the 3 minute results; and hold times of between 7 and 10 minutes will be represented by the 10 minute results. FIG. 4 demonstrates the changes in cell volume as a function of temperature upon cooling to various subzero hold temperatures ranging from −3° C. to −30° C., holding for a duration, and then cooling at 325° C./min to the storage temperature. The results shown are for (a) 0.5 min., (b) 3 min., and (c) 10 min. hold times. Cells showed a progressive decrease in cell volume upon cooling. Cells only held for 0.5 minutes at the subzero temperature did not reach the same volumes as those held for 3 or 10 minutes at −3° C. and −35° C. These results suggest that the cells have not had sufficient amount of time to dehydrate with a hold time of 0.5 minutes, as opposed to hold times greater than 3 minutes, for both high and low subzero hold temperatures. This data also indicates that the cells would have a higher amount of supercooling at these outlying hold temperatures due to the lack of cellular dehydration. Also, with lower concentrations of $[KCl]_i$, it is possible that the cells would not be subjected to high solution effects.

Supercooling During Cooling

Figure 5:
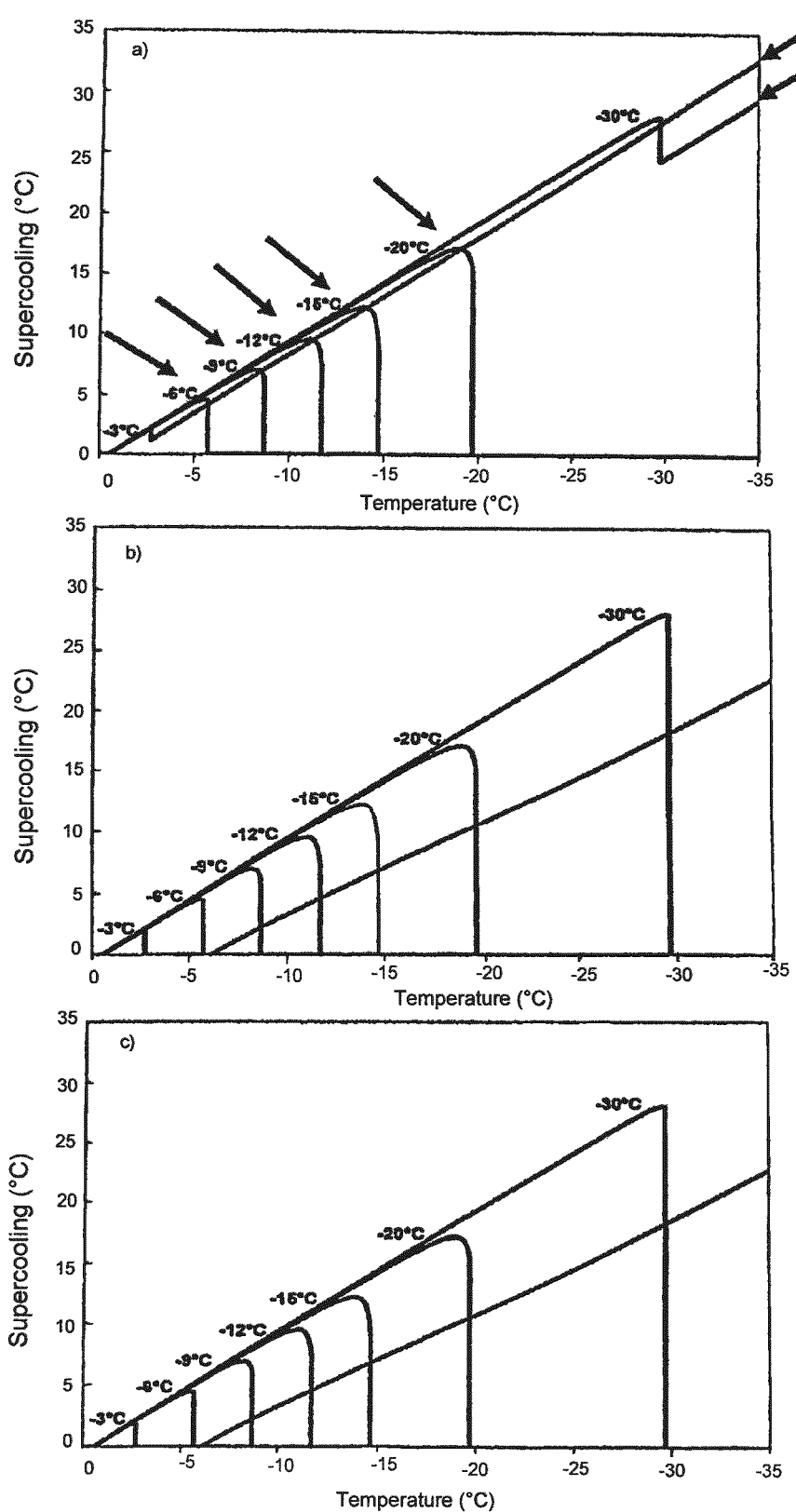
FIG. 5. Examples of simulations of intracellular supercooling as a function of temperature for TF-1 cells in the stepped method, cooled according to Newton's Law of Cooling (constant=$6.6$ s$^{-1}$) to various subzero hold temperatures ($-3°$ C. to −40° C.) and held at that temperature for (a) 0.5 min., (b) 3 min., and (c) 10 min., prior to rapid cooling at 325° C./min. Arrows indicate maximum supercooling.

FIG. 5 demonstrates the changes in amount of intracellular supercooling as a function of temperature upon cooling to various subzero hold temperatures ranging from −3° C. to −30° C., prior to being cooled rapidly at 325° C./min. Results shown are for (a) 0.5 min., (b) 3 min., and (c) 10 min. hold times. Supercooling of up to 10° C. occurs for all the hold times at hold temperatures down to −12° C. This indicates that supercooling plays a key role in potential injury during freezing to lower subzero hold temperatures. At these lower temperatures, cells were exposed to increasingly supercooled conditions of up to 30° C. of supercooling at −40° C.

$[KCl]_i$ During Cooling

Figure 6:
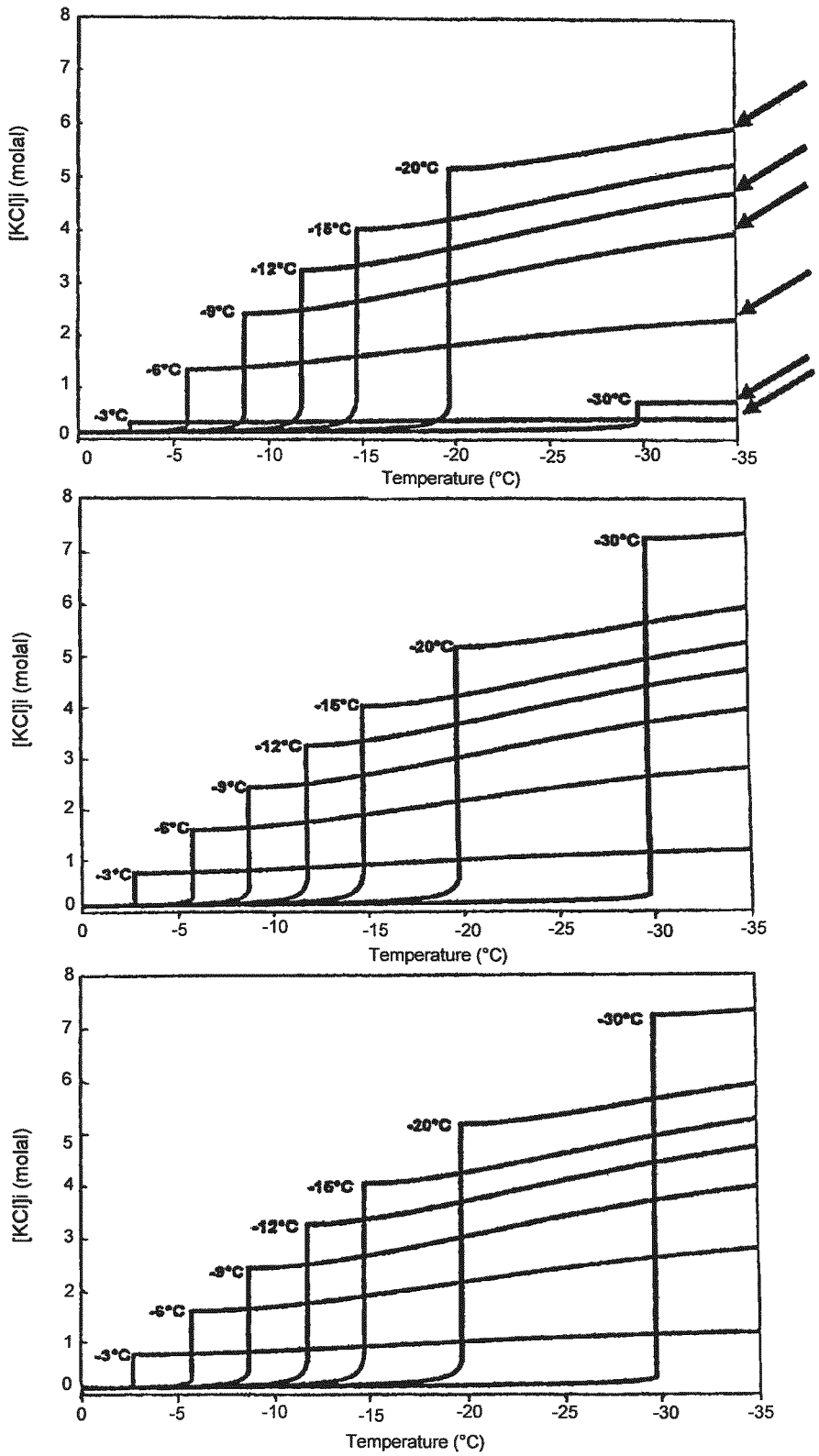
FIG. 6. Example simulations of $[KCl]_i$ as a function of temperature for TF-1 cells in the stepped method, cooled according to Newton's Law of Cooling (constant=6.6 s$^{-1}$) to various subzero hold temperatures (−3° C. to −40° C.) and held at that temperature for (a) 0.5 min., (b) 3 min., and (c) 10 min., prior to rapid cooling at 325° C./min. Arrows indicate maximum $[KCl]_i$.

FIG. 6 demonstrates the changes in $[KCl]_i$ as a function of temperature upon cooling to various subzero hold temperatures ranging from −3° C. to −30° C., prior to being cooled rapidly at 325°/min. The results shown are for (a) 0.5 min., (b) 3 min., and (c) 10 min. hold times. Cells cooled to lower subzero hold temperatures showed increasing concentrations of $[KCl]_i$, with the highest concentration for cells cooled to −30° C. and held for greater than 3 minutes. This correlates with the gradual decrease in cell volume reported in the previous section. This gradual increase in $[KCl]_i$ demonstrates the potential for increased solution effects upon cooling to the lower subzero hold temperatures. The data show similar concentrations of $[KCl]_i$ at all hold temperatures except at −3° C. and below −30° C.

Maximum Supercooling and $[KCl]_i$ During Cooling

Figure 7:
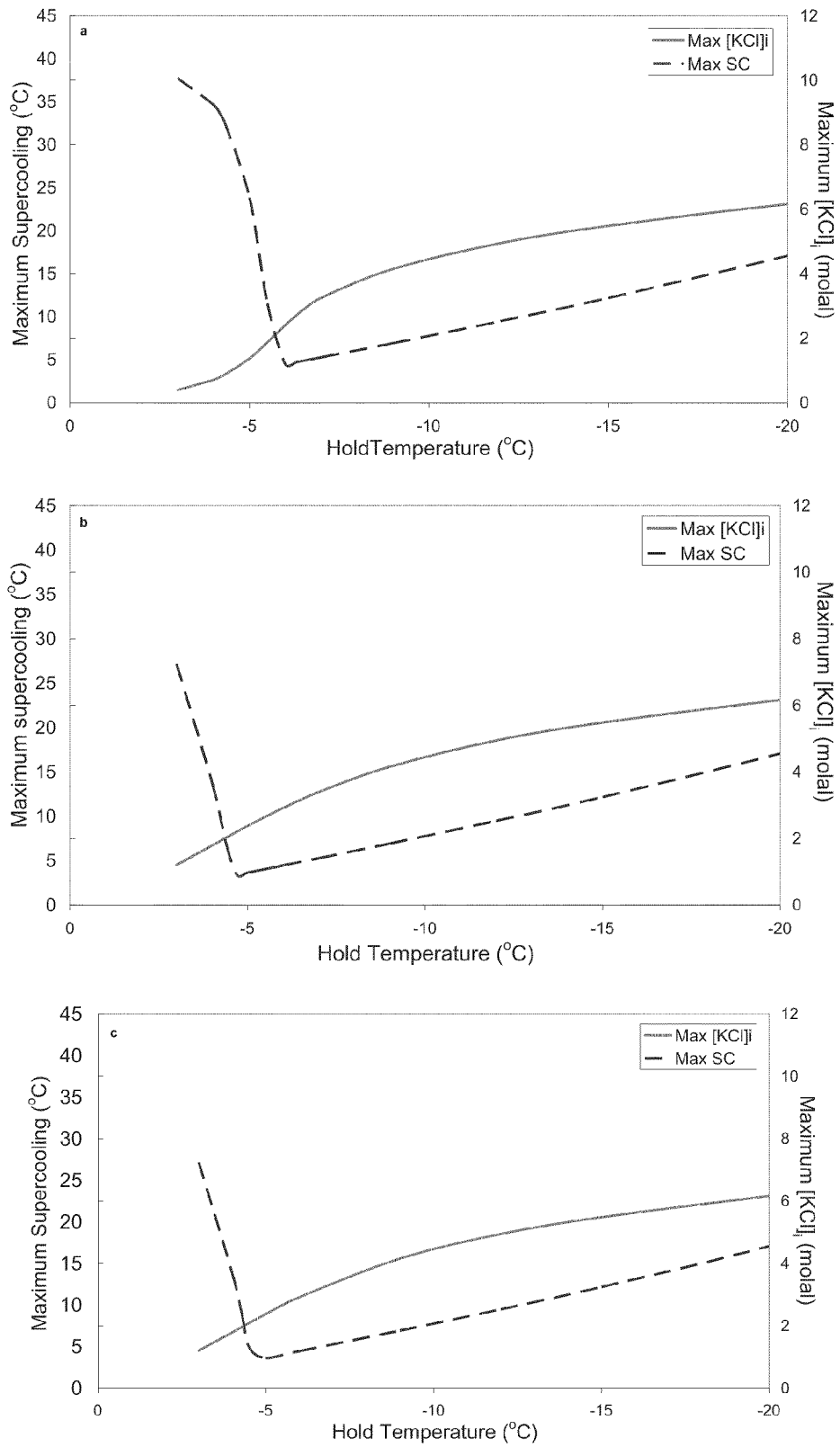
FIG. 7. Maximum $[KCl]_i$ and maximum intracellular supercooling as a function of temperature from example simulations for TF-1 cells in the stepped method, cooled to various subzero hold temperatures and held at that temperature for (a) 0.5 min. (b) 3 min. and (c) 10 min. prior to rapid cooling at 325° C./min.

The maximum amount of supercooling was calculated as the highest amount of supercooling which occurred throughout the cooling profile for each hold temperature. FIG. 5a shows calculated amount of supercooling as a function of temperature for TF-1 cells with arrows indicating where the maximum supercooling was determined for the various hold temperatures. The maximum amount of supercooling was calculated and graphed as a function of hold temperature (FIG. 7). Results are shown for (a) 0.5 min., (b) 3 min., and (c) 10 min. hold times. The maximum supercooling obtained appears to be the primary contributor to potential injury, which suggests that a target hold temperature between −6° C. to −12° C. would lead to high levels of survival because the supercooling does not exceed 10° C. Cells held for 0.5 minutes have a more narrow range of optimal hold temperatures, limited by the amount of supercooling. These results correlate with the lack of cellular dehydration discussed in the previous sections.

Figure 8:
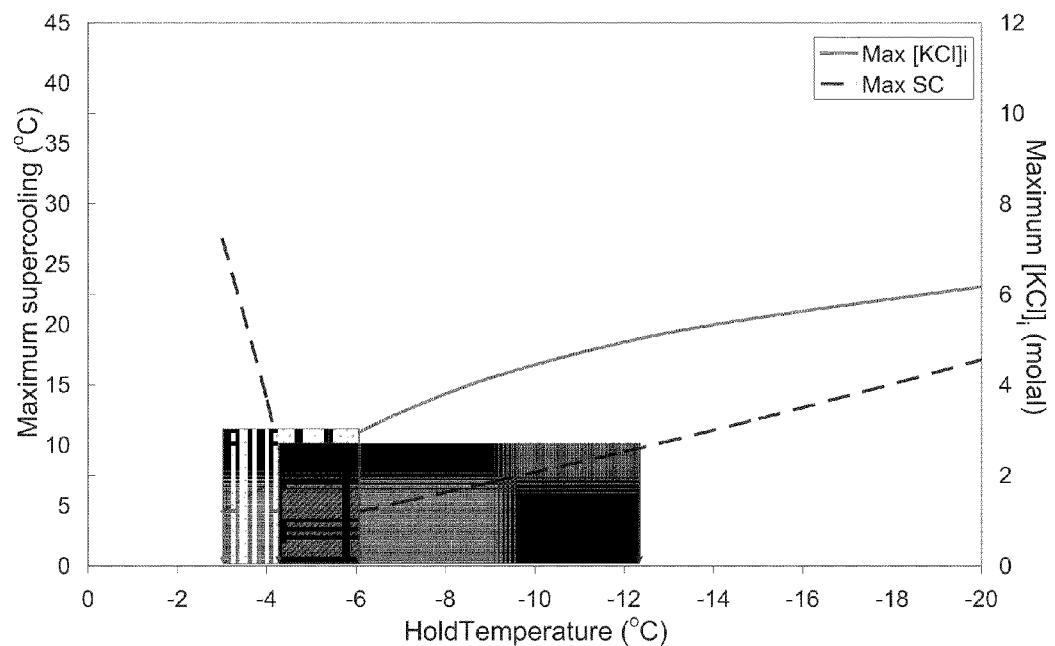
FIG. 8. Maximum $[KCl]_i$ and maximum supercooling as a function of temperature from example simulations for TF-1 cells in the stepped method, cooled to various subzero hold temperatures and held at that temperature for 3 min. prior to rapid cooling at 325° C./min. The shaded box indicates the optimal hold temperature of between −4° C. and −6° C. based on 10° C. maximum intracellular supercooling and 3 M maximum intracellular $[KCl]_i$.

The maximum amount of $[KCl]_i$ was calculated as the highest concentration of intracellular KCl which occurred throughout the cooling profile for each hold temperature. FIG. 6a shows the $[KCl]_i$ as a function of temperature for TF-1 cells, with arrows indicating where the maximum $[KCl]_i$ was determined for the various hold temperatures. The levels of maximum $[KCl]_i$ for cells held for 0.5, 3 and 10 minutes gradually increase from −3° C. to −20° C. (FIG. 7). The slope between −3° C. and −6° C. varies for cells held for 0.5 minutes and 3 to 10 minutes, suggesting that at hold temperatures between −3° C. and −6° C., there may be a difference in cell recovery between hold times of 0.5 minutes and 3 to 10 minutes. For all the hold times, based on the temperature range set by the 10° C. limit to supercooling, the results suggest that the lower $[KCl]_i$ levels would result in better cell recovery. FIG. 8 shows the hold temperature ranges for cells held for 3 minutes based on 10° C. supercooling and 3 M $[KCl]_i$. This range varies between the 0.5 minute hold time and the 3 and 10 minute hold time. Based on simulations a target hold temperature of approximately −6° C. should result in the highest cell recovery for all the hold times.

These simulations suggest that supercooling plays a key role in two-step freezing and the effects of increasing solute concentrations are secondary. The optimal hold temperature for the cells is a function of the amount of time spent to cool to a specific temperature, which influences $[KCl]_i$ and intracellular supercooling.

Example 2

Experimental Correlation and Optimization of a Theoretically-Designed Cryopreservation Protocol 2.1 Introduction The simulations performed in Example 1 predicted that subzero hold temperature and time spent at that temperature were critical variables in the optimization of cryopreservation protocols. In order for simulations to be used in cryopreservation, the predictions of simulations were tested empirically. The purpose of this example was to explore the range of subzero hold temperatures and time spent at those temperatures. Two-step cooling experiments were conducted with TF-1 cells and cooling profiles leading to high or low survival were compared with those that were theoretically predicted in Example 1 to have high or low cell survival. Membrane integrity was used as an assay for freeze-thaw injury. Cooling profiles leading to high or low recovery were compared with those that were theoretically predicted.

2.2 Materials & Methods

TF-1 Cell Culture

TF-1 cells (ATCC, Manassas, Va.) were grown at 37° C. in 5% $CO_2$ in RPMI 1640 Medium Modified (ATCC) with 10% fetal bovine serum (FBS) (ATCC), and supplemented with 2 ng/mL recombinant human GM-CSF (Stemcell Technologies, Vancouver, Canada). Cells were maintained between $0.1 \times 10^6$ and $1 \times 10^6$ cells/mL, according to ATCC guidelines. Prior to experiments, cells were washed twice with serum-free RPMI media and incubated overnight. Cells were then centrifuged and re-suspended at a concentration of $4 \times 10^6$ cells/mL, which was necessary for the viability assessment program to be used.

Experimental Solutions

TF-1 cells were re-suspended in serum-free RPMI prior to the two-step freezing experiments.

Two-Step Freezing Experiments

Samples of 0.2 mL cell suspension, in serum-free RPMI, in glass tubes were allowed to equilibrate at room temperature for 5 minutes. Control samples were either warmed in a 37° C. water bath or cooled rapidly in liquid nitrogen. Experimental samples were individually transferred into a methanol bath preset at −3, −6, −9, −12, −15, −20, −30, and −40° C. and allowed to equilibrate for 2 minutes at that temperature prior to ice nucleation with cold forceps. After nucleation, samples were allowed to equilibrate for 3 minutes before either being thawed directly in a 37° C. water bath or cooled rapidly in liquid nitrogen. Samples were kept in liquid nitrogen for a minimum of 1 hour prior to being thawed in a 37° C. water bath. Duplicate samples were used for both the direct thaw and the liquid nitrogen conditions at each hold temperature. Each experiment was repeated in triplicate.

The two-step freezing experiments were repeated with varying hold times. Cells were cooled to a hold temperature of −5, −7, −9, −12, −15, or −25° C. and allowed to equilibrate for 2 minutes prior to ice nucleation with cold forceps. After nucleation, samples were allowed to equilibrate for 0.5 to 10 minutes before either being thawed directly in a 37° C. water bath or cooled rapidly in liquid nitrogen. Samples were kept in liquid nitrogen for a minimum of 1 hour prior to being thawed in a 37° C. water bath. Duplicate samples were used for both the direct thaw and the liquid nitrogen conditions at each hold temperature. Each experiment was repeated in triplicate.

Viability Assessment

Cell viability was assessed by a membrane integrity assay. The assay was performed by incubating cells with SYTO® 13 (Molecular Probes, Eugene, Oreg.) and ethidium bromide (EB) (Sigma, Mississauga, Canada) (Yang, 1998). Syto 13 permeates the cell membrane of all cells and complexes with DNA and it fluoresces green under UV exposure. EB penetrates cells with a damaged plasma membrane and also complexes with DNA fluorescing red under UV conditions. The dual stain allows for differentiation between cells with and without intact plasma membranes.

The Syto/EB stain was prepared using 40 μL of 2.5 mM EB stock solution and 10 μL of 5 mM Syto® 13 stock solution mixed with 350 μL 1× phosphate-buffered saline (PBS). Final concentrations were 0.25 mM EB and 0.125 mM Syto. Twenty μL of stain was added to each sample and allowed to incubate for 2 minutes at room temperature. Fluorescent images were captured using a Leitz Dialux 22 fluorescence (440-480 nm) microscope (Leitz, Germany) fitted with a PIX-ERA DiRactor (Pixera Corporation, Los Gatos, Calif., USA) digital camera. The Viability Assessment Program (The Great Canadian Computer Company, Spruce Grove, Canada), which counts red versus green pixels was used to quantify cell membrane integrity from digital images (Jomha, 2003). This method measures membrane integrity of the cell remaining after experimental treatment.

2.3 Results

Varying Hold Temperature

Figure 9:
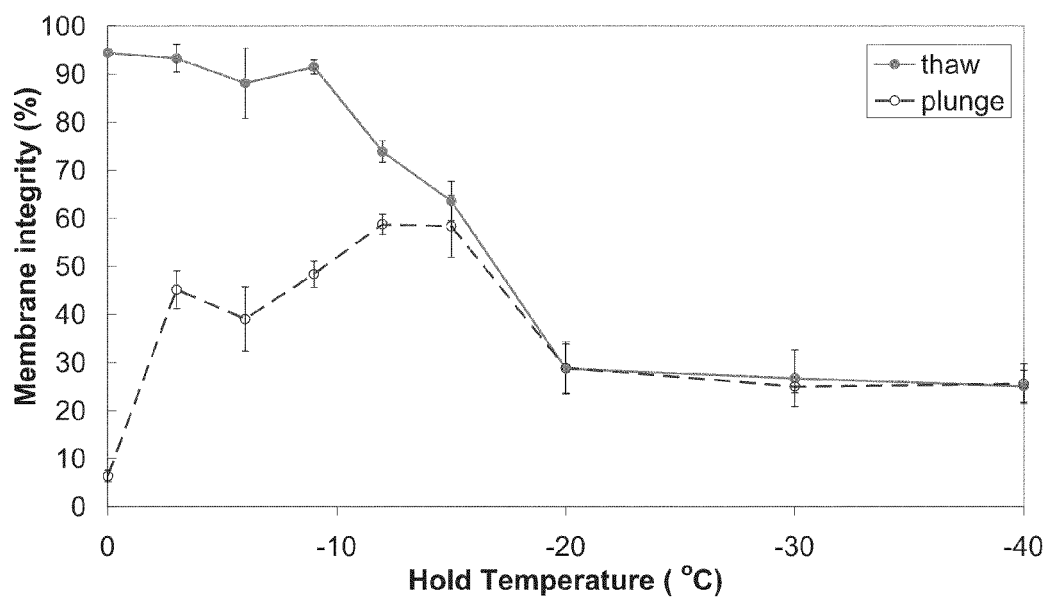
FIG. 9. Membrane integrity for TF-1 cells (±SEM) in serum-free RPMI media cooled using the stepped method to various subzero hold temperatures from room temperature by immersion in a constant-temperature bath, held 3 minutes, and then either thawed directly (upper curve) or cooled rapidly at 325° C./min in liquid nitrogen (lower curve) before being thawed.

TF-1 cells were suspended in serum-free RPMI, cooled to various hold temperatures down to −40° C. and held for 3 minutes, prior to being thawed directly or cooled rapidly in liquid nitrogen (FIG. 9). Cells cooled in liquid nitrogen showed comparable results for membrane integrity to cells directly thawed from temperatures ranging from −15° C. to −40° C. Cells thawed directly from the hold temperatures showed a 50% decrease in membrane integrity by −17° C., indicating that a major portion of cells were damaged prior to being cooled rapidly in liquid nitrogen (FIG. 9). However, this membrane damage occurred at a higher subzero hold temperature for cells cooled at 0.9° C./min. The maximum recovery of 58.8±6.5% was seen for TF-1 cells cooled to −12° C. or −15° C. before being cooled rapidly in liquid nitrogen. This recovery was comparable with 63.7% recovery obtained after conventional cooling at a constant rate of 0.9° C./min in 10% DMSO/RPMI.

Varying Experimental Hold Time

Figure 10:
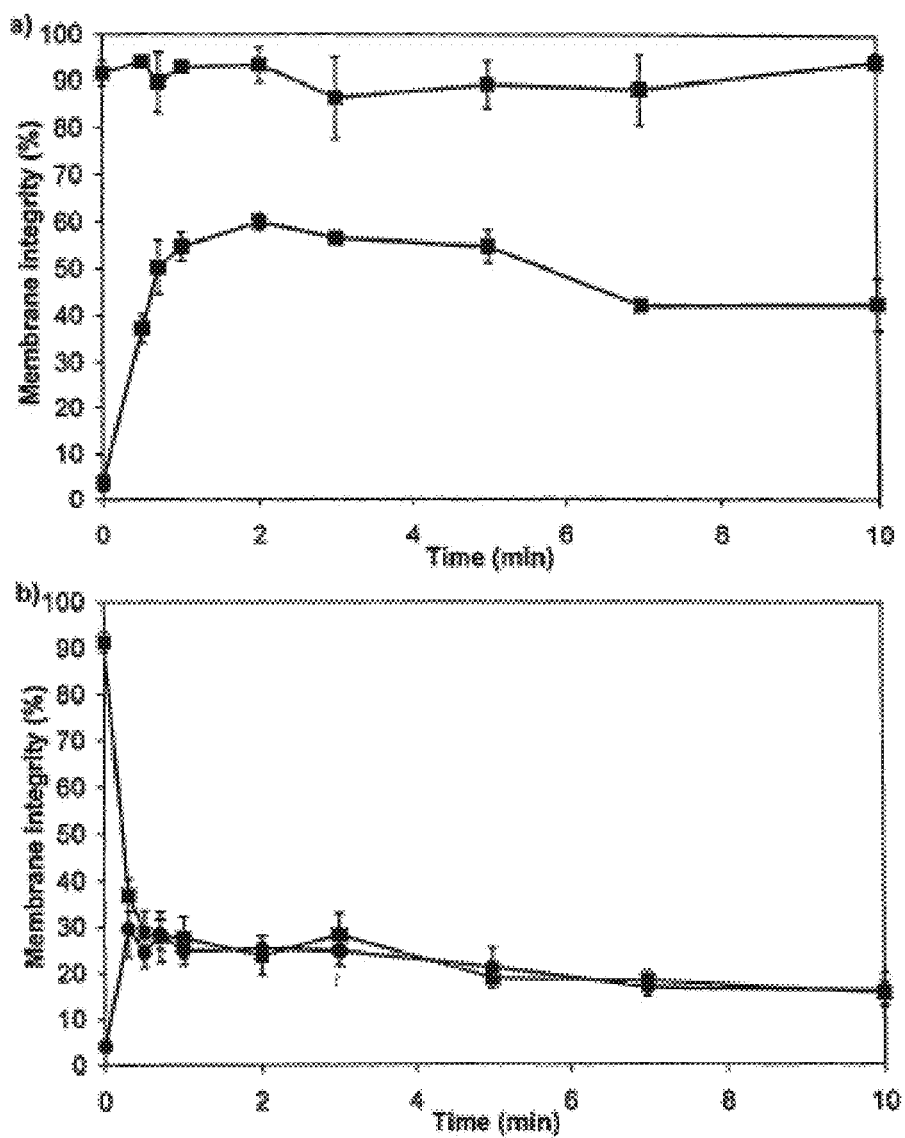
FIG. 10. The membrane integrity of TF-1 cells (±SEM) in serum-free RPMI media as a function of hold time for cells cooled using the stepped method to (a) −5° C. and (b) −25° C., held for a period of time before being either thawed directly (upper curves) or cooled rapidly at 325° C./min in liquid nitrogen (lower curves) before being thawed.
Figure 11:
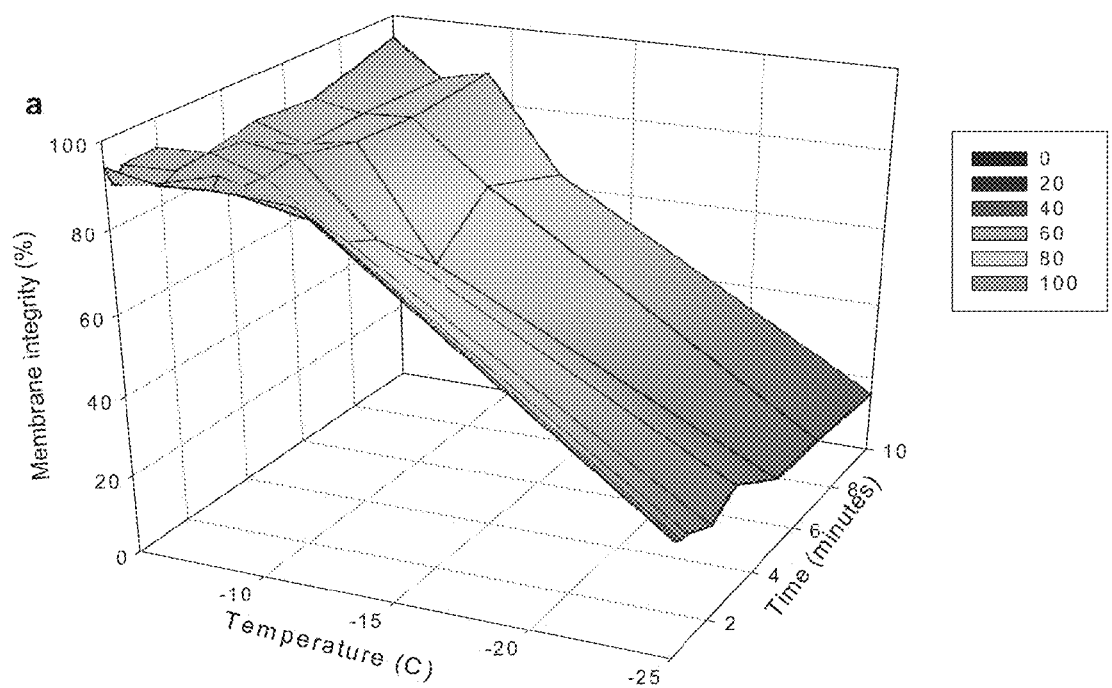
FIG. 11. Contours of membrane integrity of TF-1 cells in serum-free RPMI media after being cooled using the stepped method to various subzero hold temperatures and held for a duration ranging from 0.5 to 10 minutes before either (a) thawed directly or (b) cooled rapidly at 325° C./min in liquid nitrogen prior to thawing.
Figure 11:
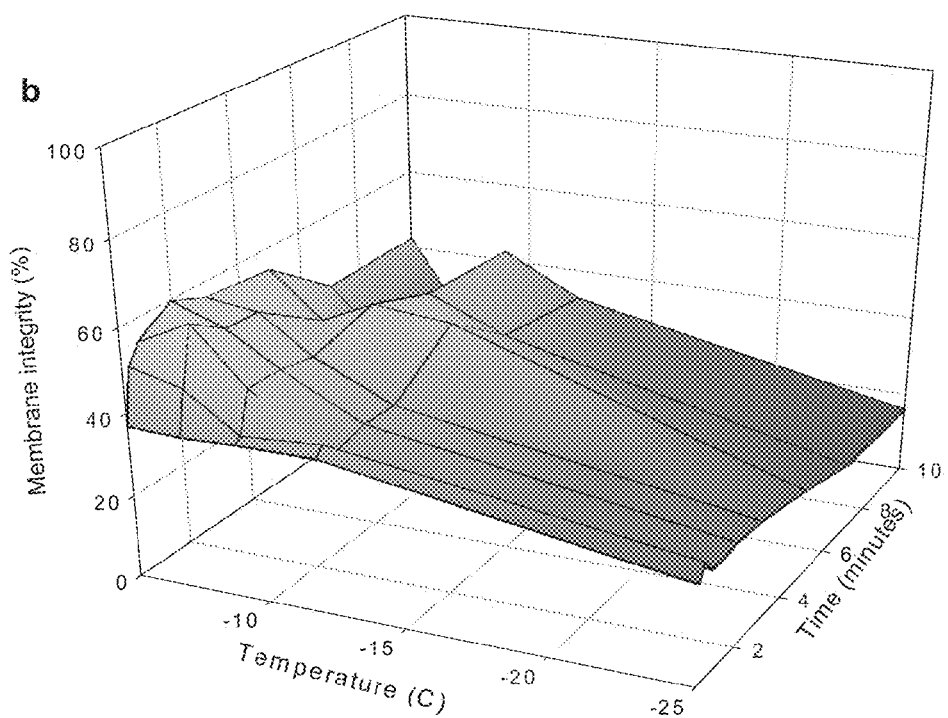
Figure 12:
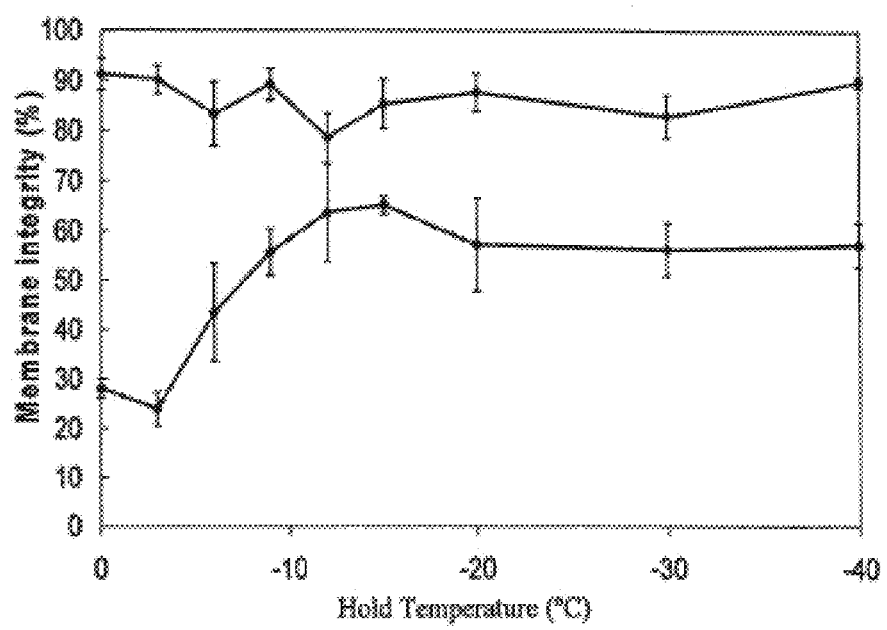
FIG. 12. Membrane integrity of TF-1 cells in 10% DMSO cooled at 1° C./min to various subzero temperatures and then either thawed directly (upper curve) or cooled rapidly at 325° C./min in liquid nitrogen (lower curve) before being thawed.

TF-1 cells were cooled to hold temperatures of −5, −7, −9, −12, −15, or −25° C. and allowed to equilibrate for 2 minutes prior to ice nucleation with cold forceps. After nucleation, samples were held at that temperature for varying times (0.3, 0.5, 0.7, 1, 2, 3, 5, 7, and 10 minutes) before either being thawed directly in a 37° C. water bath or cooled rapidly in liquid nitrogen. FIG. 10a shows the membrane integrity of TF-1 cells as a function of hold time for cells cooled to −5° C., held and cooled rapidly in liquid nitrogen. Comparable results of membrane integrity were obtained for cells held at −7° C. to −9° C. (results not shown). However there was minimal membrane integrity for cells held below −25° C. (data shown in FIG. 10b). Cells that were directly thawed from the subzero hold temperatures after being held showed progressive decrease in membrane integrity based on reduced temperature and increased duration of hold time (FIG. 11a). Results indicated a high percentage of membrane integrity of 55 to 60%, when cells were held for 1-5 minutes at high subzero hold temperatures. Cells cooled from room temperature to −5° C. and −7° C. and held for 1-3 minutes, prior to plunging into liquid nitrogen resulted in the highest percentage of membrane integrity of approximately 60% (FIG. 11b). A hold time of greater than 5 minutes resulted in a marked decrease in cell survival. This data indicates that there is a zone of subzero hold temperatures (−5° C. to −15° C.), when held for 1-3 minutes, which confers protection against injury comparable to DMSO.

With larger sample volumes, different cell types and different compositions of the intracellular and extracellular solutions, hold temperatures and hold times may vary over larger ranges, for instance 1 to 30 minutes between −3 and −30° C. For instance, in the present examples 200 microliter samples were used. If one uses larger volumes, such 50 ml standard bags for umbilical cord blood samples, the latent heat of fusion effects will differ and may deviate from Newton's Law of Cooling, which would effet hold times. In which case numerical values of the temperature of the sample as a function of time would be obtained for the temperature profile, by for instance putting a thermocouple into the bag.

5.4 Correlation with Theoretically-Designed Protocol Discussion of Experimental Results The experimental results for cryopreserving TF-1 cells without cryoprotectants indicate that cells can be cryopreserved without DMSO. This data indicates that there is a zone of subzero hold temperatures (−5° C. to −15° C.), when held for 1-3 minutes, which confers comparable protection against injury to the standard 10% DMSO/RPMI solution, previously reported in Ross-Rodriquez. This range would constitute an optimal subzero temperature range for these hold times based on experimental results.

Comparison of Theoretical and Experimental Results

Simulations were done based on an empirical approach to cryopreservation, two-step freezing, which can be used to examine the role of exposure to subzero hold temperatures and exposure time. The cooling rates used in the two-step freezing protocol are, in some instances, governed by Newton's Law of Cooling and were determined experimentally in Example 1. Cells were exposed to increasingly supercooled conditions up to 30° C. of supercooling at a temperature of −40° C. Supercooling appears to be a primary indicator of potential freezing injury due to intracellular freezing. In these experiments, the inventors found that beyond 10° C. of supercooling, cell viability was not optimized for TF-1 cells. The proposed target hold temperature was suggested to be between −4° C. and −12° C., as supercooling was restricted to less than 10° C., which is comparable to the range determined empirically. Also, based on levels of intracellular KCl ([KCl]$_i$), it was suggested that the higher subzero hold temperature would have the lowest potential for solution effects based on the lack of cell dehydration, which was also supported by this data.

Two-step freezing experiments demonstrated a high percentage of membrane integrity for TF-1 cells when cells were cooled to between −5° C. and −12° C. and held for 1-5 minutes. These hold temperatures corresponded with the theoretical values of 5° C. to 10° C. supercooling, which suggested that a certain amount of supercooling is necessary to achieve a higher viability (Diller, 1975). However, this also supports the belief that excessive supercooling may lead to damage as a result of intracellular ice formation.

Based on the simulations, the duration of time the cells were held at the subzero hold temperature was also considered an important factor. When cells were held for 0.5 minutes, they did not have sufficient time to dehydrate and reach the same volume as cells held for greater than 2 minutes. This excess intracellular water may have caused damage by forming ice upon subsequent cooling. According to the two-step freezing experiments, cells held for 2 minutes at −5° C. and for 5 minutes at −12° C., had the highest cell recovery. Those held for 10 minutes may have been exposed to high concentrations of solutes for a duration which was damaging. Simulations from Example 1 predicted that there was no difference in [KCl]$_i$ concentrations and supercooling between hold times down to −25° C. The experimental results demonstrated that the differences in membrane integrity between the hold times may depend on the duration of exposure, which is consistent with the theoretical results.

For all the hold times, simulations predicted a progressive increase in [KCl]$_i$ upon cooling to lower hold temperatures down to −25° C. for cells held for 0.5 minutes. The experimental results for cells thawed directly from subzero hold temperatures demonstrated a decline in membrane integrity with decreasing hold temperature. At low subzero hold temperatures (<−20° C.), cells directly thawed had low percentages of membrane integrity (<30%). Therefore, either the exposure time and/or the concentration of solutes may have been significant variables for freezing injury.

As will be apparent to those skilled in the art in the light of the foregoing disclosure, many alterations and modifications are possible in the practice of this invention without departing from the spirit or scope thereof.

While the present invention has been described with reference to what is presently considered to be a preferred embodiment, it is to be understood that the invention is not limited to the disclosed embodiment. To the contrary, the invention is intended to cover various modifications and equivalent arrangements included within the spirit and scope of the appended claims. It should be noted the application is intended to encompass obvious chemical equivalents of the cells, tissues or other components or parameters of the invention as described herein, which are equivalents that produce the same or equivalent desired result for a particular feature of the invention.

All publications, patents, and patent applications are herein incorporated by reference in their entireties, to the same extent as if each individual publication, patent, or patent application was specifically and individually indicated to be incorporated by reference in its entirety.

TABLE 1

| | Extracellular | Intracellular |
|---|---|---|
| a) Isotonic solution composition | | |
| NaCl | 0.171 molal | 0.010 molal |
| KCl | 0.005 molal | 0.128 molal |
| Protein | 0 | 0.004 molal |
| Total Osmolality | 0.301 osm/kg | 0.301 osm/kg |
| b) Osmotic parameters | | |
| Isotonic volume | 776 μm³ | |
| Inactive fraction | 0.353 | |
| $L_p$ at 20° C. | 0.342 μm/min/atm | |
| Activation Energy for $L_p$ | 13.4 kcal/mol | |
| c) Cooling profiles | | |
| k | 6.6 s$^{-1}$ | |

| | $K_{diss}$ | $B2_i$ (molal$^{-1}$) | B3 (molal$^{-2}$) |
|---|---|---|---|
| d) Solution thermodynamic parameters | | | |
| NaCl | 1.702 | 0.0299 | — |
| KCl | 1.742 | — | — |
| Protein | — | 49.3 | 3.07 × 10⁴ |

REFERENCES

J. F. Abrahamsen, A. M. Bakken, O. Bruserud, Cryopreserving human peripheral blood progenitor cells with 5-percent rather than 10-percent DMSO results in less apoptosis and necrosis in CD34+cells, Transfusion 42 (2002) 1573-1580.

J. P. Acker, A. Larese, h. Yang, A. Petrenko, L. E. McGrann, Intracellular ice formation is affected by cell interactions, Cryobiology 38 (1999) 363-371.

J. P. Acker, J. Pasch, I. Heschel, G. Rau, L. E. McGann, Comparison of optical measurement and electrical measurement techniques for the study of osmotic responses of cell suspensions, Cryo-Letters 20 (1999) 315-324.

J. P. Acker, L. E. McGann, Cell-cell contact affects membrane integrity after intracellular freezing, Cryobiology 40 (2000) 54-63.

J. P. Acker, L. E. McGann, Membrane damage occurs during the formation of intracellular ice, Cryo-Letters 22 (2001) 241-254.

J. P. Acker, J. A. W. Elliott, L. E. McGann, Intercellular ice propagation: Experimental evidence for ice growth through membrane pores, Biophysical Journal 81 (2001) 1389-1397).

J. P. Acker, L. E. McGann, Innocuous Intracellular ice improves survival of frozen cells, Cell Transplantation 11 (2002) 563-571.

B. Alberts, D. Bray, J. Lewis, M. Raff, K. Roberts, J. D. Watson, Molecular biology of the cell (Garland Publishing, Inc, New York & London, 1994) 1294.

D. S. Allan, M. Keeney, K. Howson-Jan, M. Bhatia, D. R. sutherland, I. Chin-Yee, Number of viable CD34+cells reinfused predicts enfraftment in autologous hematopoietic stem cell transplantation., Blood 96 (2000) 381a-381a.

W. J. Armitage, P. Mazur, Osmotic tolerance of human-granulocytes, American Journal of Physiology 247 (1984) C373-C381.

Bannerman, R. B., J. A. W. Elliott, et al. (2005). "A multi-solute osmotic virial equation for solutions of interest in biology." Biophysical Journal (submitted for publication Aug. 18, 2005).

F. Beaujean, J. H. Bourhis, C. Bayle, H. Jouault, M. Divine, C. Rieux, M. Janvier, C. Le Forestier, J. L. Pico, Successful cryopreservation of purified autologous CD34(+) cells: influence of freezing parameters on cell recovery and engraftment, Bone Marrow Transplantation 22 (1998) 1091-1096.

C. T. Benson, C. Liu, D. Y. Gao, E. S. Critser, J. D. Benson, J. K. Critser, Hydraulic conductivity (L-p) and its activation energy (E-a), cryoprotectant agent permeability (P-s) and its E-a, and reflection coefficients (sigma) for golden hamster individual pancreatic islet cell membranes, Cryobiology 37 (1998) 290-299.

C7043, Stem Cell Laboratory Endpoints, in: S.C. Laboratoy (Ed.), (Canadian Blood Services, Edmonton Centre, 2003).

J. M. Davis, S. D. Rowley, H. G. Braine, S. Piantadosi, G. W. Santos, Clinical toxicity of cryopreserved bone-marrow graft infusion, Blood 75 (1990) 781-786.

D. A. T. Dick, L. M. Lowenstein, Osmotic Equilibria in Human Erythrocytes Studied by Immersion Refractometry., Proceedings of the Royal Society of Londong, Series B 149 (1958) 241-256.

K. R. Diller, Intracellular freezing—effect of extracellular supercooling, Cryobiology 12 (1975) 480-485.

C. Donaldson, W. J. Armitage, P. A. DenningKendall, A. J. Nicol, B. A. Bradley, J. M. Hows, Optimal cryopreservation of human umbilical cord blood, Bone Marrow Transplantation 18 (1996) 725-731.

M. J. Egorin, E. G. Zuhowski, D. M. Rosen, D. L. Sentz, J. M. Covey, J. L. Eiseman, Plasma pharmacokinetics and tissue distribution of 17-(allylamino)-17-demethoxygeldanamycin (NSC 330507) in CD2F1 micel, Cancer Chemotherapy and Pharmacology 47 (2001) 291-302.

S. L. Ebertz, Fundamental cryobiology of cells from a bioengineered human corneal equivalent, Doctor of Philosophy, Medical Sciences—Laboratory Medicine and Pathology, University of Alberta, 2002.

S. L. Ebertz, L. E. McGann, Osmotic parameters of cells from a bioengineered human corneal equivalent and consequences for cryopreservation, Cryobiology 45 (2002) 109-117.

J. A. W. Elliott, L. E. McGann, S. Hakda, K. Porter, R. C. Bannerman, Thermodynamics in cryobiology: Limitations of the Boyle van't Hoff equation., Cryobiology 45 (2002) 252. H. Y. Elmoazzen, J. A. W. Elliott, L. E. McGann, The effect of temperature on membrane hydraulic conductivity, Cryobiology 45 (2002) 68-79.

H. Y. Elmoazzen (Speaker), J. A. W. Elliott and L. E. McGann, "A new look at an old topic: Osmotic transport across cell membranes", Cryo 2005, Society for Cryobiology Annual Meeting, Minneapolis, Minn., USA, Jul. 24-27, 2005 abstract to be published in the December 2005 issue of Cryobiology.

H. Y. Elmoazzen (Speaker), J. A. W. Elliott and L. E. McGann, "Implications of dilute and non-dilute solution assumptions in osmotic transport models", Cryo 2004, Society for Cryobiology Annual Meeting, Beijing, China, Jul. 15-19, 2004—abstract published in Cryobiology 49(3), 301 (2004).

J. Farrant, S. C. Knight, L. E. McGann, J. O'Brien, Optimal recovery of lymphocytes and tissue culture cells following rapid cooling, Nature 249 (1974) 452-453.

J. Farrant, C. A. Walter, H. Lee, L. E. McGann, Use of two-step cooling procedures to examine factors influencing cell survival following freezing and thawing, Cryobiology 14 (1977) 273-286.

D. Y. Gao, C. Liu, C. T. Benson, J. Liu, E. S. Critser, J. K. Critser, L. E. McGann, S. Lin, Theoretical and experimental analyses of optimal experimental design for determination of hydraulic conductivity of cell membrane., in: L. J. Hayes, R. B. Roemer (Eds.), Advances in heat and mass transfer in biological systems., Vol. 288 (American Society of Mechanical Engineers., New York, N.Y., 1994) 151-158.

D. Y. Gao, Q. Chang, C. Liu, K. Farris, K. Harvey, L. E. McGann, D. English, J. Jansen, J. K. Critser, Fundamental cryobiology of human hematopoietic progenitor cells I: Osmotic characteristics and volume distribution, Cryobiology 36 (1998) 40-48.

D. Y. Gao, J. K. Critser, Mechanisms of cryoinjury in living cells, Ilar J 41 (2000) 187-196.

J. A. Gilmore, L. E. McGann, E. Ashworth, J. P. Acker, J. P. Raath, M. Bush, J. K. Critser, Fundamental cryobiology of selected African mammalian spermatozoa and its role in biodiversity preservation through the development of genome resource banking, Animal Reproduction Science 53 (1998) 277-297.

N. B. Grover, J. Naaman, S. Ben-Sasson, F. Doljanski, Electrical sizing of particles in suspensions. I: Theory, Biophysical Journal 9 (1969) 1398-1414.

N. B. Grover, J. Naaman, S. Ben-Sasson, F. Doljanski, Electrical sizing of particles in suspensions. III: Rigid spheroids and red blood cells, Biophysical Journal 12 (1972) 1099-1117.

N. B. Grover, J. Naaman, S. Ben-Sasson, F. Doljanski, E. Nadav, Electrical sizing of particles in suspensions. II: Experiments with rigid spheres, Biophysical Journal 9 (1969) 1415-1425.

P. Halle, O. Tournilhac, W. Knopinska-Posluszny, J. Kanold, P. Gembara, N. Boiret, C. Rapatel, M. Berger, P. Travade, S. Angielski, J. Bonhomme, F. Demeocq, Uncontrolled-rate freezing and storage at −80 degrees C., with only 3.5-percent DMSO in cryoprotective solution for 109 autologous peripheral blood progenitor cell transplantations, Transfusion 41 (2001) 667-673.

H. G. Hempling, S. Thompson, A. Dupre, Osmotic properties of human lymphocyte, Journal of Cellular Physiology 93 (1977) 293-302.

A. Hubei, J. Norman, T. B. Darr, Cryobiophysical characteristics of genetically modified hematopoietic progenitor cells, Cryobiology 38 (1999) 140-153.

C. J. Hunt, S. E. Armitage, D. E. Pegg, Cryopreservation of umbilical cord blood: 1. Osmotically inactive volume, hydraulic conductivity and permeability of CD34(+) cells to dimethyl, sulphoxide, Cryobiology 46 (2003) 61-75.

C. J. Hunt, S. E. Armitage, D. E. Pegg, Cryopreservation of umbilical cord blood: 2. Tolerance of CD34(+) cells to multimolar dimethyl sulphoxide and the effect of cooling rate on recovery after freezing and thawing, Cryobiology 46 (2003) 76-87.

F. P. Incopera, D. P. Dewitt, Introduction to heat transfer (John Wiley & Sons, New York, 2002) 892.

M. H. Jacobs, D. R. Steward, A simple method for the quantitative measurement of cell permeability, Journal of Cellular and Comparative Physiology 1 (1932) 71-82.

M. H. Jacobs, The simultaneous measurement of cell permeability to water and to dissolved substances, Journal of Cellular and Comparative Physiology 2 (1933) 427-444.

J. A. Johnson, T. A. Wilson, Osmotic volume changes induces by a permeable solute, Journal of Theoretical Biology 17 (1967) 304-311.

N. M. Jomha, P. C. Anoop, J. A. Elliott, K. Bagnall, L. E. McGann, Validation and reproducibility of computerised cell-viability analysis of tissue slices, BMC Musculoskelet Disord 4 (2003) 5.

Y. Katayama, T. Yano, A. Bessho, S. Deguchi, K. Sunami, N. Mahmut, K. Shinagawa, E. Omoto, S. Makino, T. Miyamoto, S. Mizuno, T. Fukuda, T. Eto, T. Fujisaki, Y. Ohno, S. Inaba, Y. Niho, M. Harada, The effects of a simplified method for cryopreservation and thawing procedures on peripheral blood stem cells, Bone Marrow Transplantation 19 (1997) 283-287.

O. Kedem, A. Katchalsky, Thermodynamic Analysis of the Permeability of Biological Membranes to Non-Electrolytes, Biochimica Et Biophysica Acta 27 (1958) 229-246.

T. Kitamura, T. Tange, T. Terasawa, S. Chiba, T. Kuwaki, K. Miyagawa, Y. F. Piao, K. Miyazono, A. Urabe, F. Takaku, Establishment and characterization of a unique human cell-line that proliferates dependently on GM-CSF, IL-3, or erythropoietin, Journal of Cellular Physiology 140 (1989) 323-334.

T. Kitamura, A. Tojo, T. Kuwaki, S. Chiba, K. Miyazono, A. Urabe, F. Takaku, Identification and analysis of human erythropoietin receptors on a factor-dependent cell-line, TF-1, Blood 73 (1989) 375-380.

Knight, S. C., J. Farrant, et al. (1977). "Storage of human lymphocytes by freezing in serum alone." Cryobiology 14(1): 112-5.

A. Kolonics, A. Apati, J. Janossy, A. Brozik, R. Gati, A. Schaefer, M. Magocsi, Activation of Raf/ERK1/2 MAP kinase pathway is involved in GM-CSF-induced proliferation and survival but not in erythro Krause, D. S. (2002). "Regulation of hematopoietic stem cell fate." Oncogene, 21(21): 3262-9.

S. P. Leibo, J. Farrant, P. Mazur, M. G. Hanna, Jr., L. H. Smith, Effects of freezing on marrow stem cell suspensions: interactions of cooling and warming rates in the presence of PVP, sucrose, or glycerol, Cryobiology 6 (1970) 315-332.

S. P. Leibo, Freezing damage of bovine erythrocytes—simulation using glycerol concentration changes at subzero temperatures, Cryobiology 13 (1976) 587-598.

C. Liu, C. T. Benson, D. Y. Gao, B. W. Haag, L. E. Mcgann, J. K. Critser, Water permeability and Its activation-energy for individual hamster pancreatic-islet cells, Cryobiology 32 (1995) 493-502.

J. Liu, J. A. Christian, J. K. Critser, Canine RBC osmotic tolerance and membrane permeability, Cryobiology 44 (2002) 258-268.

J. E. Lovelock, The Haemolysis of Human Red Blood-Cells by Freezing and Thawing, Biochimica et Biophysica Acta 10 (1953) 414-426.

Lucke, B. and M. McCutcheon (1932). "The Living Cell as an Osmotic System and its Permeability to Water." Physiological Reviews 12: 68-139.

M. Marone, G. Scambia, G. Bonanno, S. Rutella, D. de Ritis, F. Guidi, G. Leone, L. Pierelli, Transforming growth factor-beta 1 transcriptionally activates CD34 and prevents induced differentiation of TF-1 cells in the absence of any cell-cycle effects, Leukemia 16 (2002) 94-105.

P. Mazur, Kinetics of water loss from cells at subzero temperatures and the likelihood of intracellular freezing, The Journal of General Physiology 47 (1963) 347-369.

P. Mazur, The role of cell membranes in the freezing of yeast and other cells, Annals of the New York Academy of Science. 125 (1965) 658-676.

P. Mazur, S. P. Leibo, E. H. Chu, A two-factor hypothesis of freezing injury. Evidence from Chinese hamster tissue-culture cells, Experimental Cell Research 71 (1972) 345-355.

P. Mazur, Role of Intracellular Freezing in Death of Cells Cooled at Supraoptimal Rates, Cryobiology 14 (1977) 251-272.

P. Mazur, U. Schneider, Osmotic responses of preimplantation mouse and bovine embryos and their cryobiological implications, Cell Biophysics 8 (1986) 259-285.

L. E. McGann, J. Farrant, Survival of tissue culture cells frozen by a two-step procedure to −196 degrees C. 1. Holding temperature and time, Cryobiology 13 (1976) 261-268.

L. E. McGann, Differing actions of penetrating and non-penetrating cryoprotective agents, Cryobiology 15 (1978) 382-390.

L. E. McGann, Optimal temperature ranges for control of cooling rate, Cryobiology 16 (1979) 211-216.

L. E. McGann, M. Grant, A. R. Turner, J. M. Turc, Osmotic limits of human-granulocytes, Cryobiology 18 (1981) 622-622.

L. E. McGann, A. R. Turner, M. J. Allalunis, J. M. Turc, Cryopreservation of human peripheral blood stem cells: optimal cooling and warming conditions, Cryobiology 18 (1981) 469-472.

L. E. McGann, N. S. Schachar, J. Heard, S. Lam, Osmotic properties of chondrocytes isolated from articular-cartilage, Cryobiology 19 (1982) 675-675.

L. E. McGann, A. Janowska-Wieczorek, A. R. Turner, L. Hogg, K. B. Muldrew, J. M. Ture, Water permeability of human hematopoietic stem-cells, Cryobiology 24 (1987) 112-119.

L. E. McGann, M. Stevenson, K. Muldrew, N. Schachar, Kinetics of osmotic water-movement in chondrocytes isolated from articular-cartilage and applications to cryopreservation, Journal of Orthopaedic Research 6 (1988) 109-115.

L. E. McGann, J. A. W. Elliott, Optimization of cryopreservation protocols using computer simulations, Cryobiology 47 (2003) 255.

J. J. McGrath, Membrane Transport Properties, in: K. R. Diller (Ed.), Low Temperature Biotechnology: emerging applications and engineering contributions (American Society of Mechanical Engineers, New York, 1988) 273-330.

Muldew K. and McGann L. E., Biophysical Journal 66 (2 Pt 1):532-541, February 1941.

L. U. Ross-Rodriguez, Using simulations to design a cryopreservation protocol for hematopoietic stem cells without DMSO., Masters of Science, Medical Sciences—Laboratory Medicine and Pathology, University of Alberta, 2003.

L. U. Ross-Rodriguez, H. Yang, J. A. W. Elliott, L. E. McGann, Using simulations to design a cryopreservation protocol for hematopoietic stem cells without DMSO, Cryobiology 47 (2003) 255.

N. C. Santos, J. Figueira-Coelho, J. Martins-Silva, C. Saldanha, Multidisciplinary utilization of dimethyl sulfoxide: pharmacological, cellular, and molecular aspects, Biochemical Pharmacology 65 (2003) 1035-1041.

D. Savitz, V. W. Sidel, A. K. Solomon, Osmotic Properties of Human Red Cells, Journal of General Physiology 48 (1964) 79-94.

G. J. Schwartz, K. R. Diller, Osmotic response of individual cells during freezing .1. Experimental volume measurements, Cryobiology 20 (1983) 61-77.

M. Shabana, J. J. Mcgrath, Cryomicroscope investigation and thermodynamic modeling of the freezing of unfertilized hamster ova, Cryobiology 25 (1988) 338-354

M. Toner, E. G. Cravalho, M. Karel, Cellular-Response of Mouse Oocytes to Freezing Stress—Prediction of Intracellular Ice Formation, Journal of Biomechanical Engineering-Transactions of the Asme 115 (1993) 169-174.

Voet, D. and J. G. Voet (1995). *Biochemistry*. New York, John Wiley & Sons, Inc.

F. T. Williams, C. C. Fordham, III, W. Hollander, Jr., L. G. Welt, A Study of the Osmotic Behaviour of the Human Erythrocyte, Journal of Clinical Investigation 38 (1959) 1587-1598.

A. V. Wolf, M. G. Brown, P. G. Prentiss, Concentrative properties of aqueous solutions, in: Weast (Ed.), Handbook of chemistry and physics (CRC Press, 1982) D-258, D-261.

E. J. Woods, J. Liu, C. W. Derrow, F. O, Smith, D. A. Williams, J. K. Critser, Osmometric and permeability characteristics of human placental/umbilical cord blood CD34(+) cells and their application to cryopreservation, Journal of Hematotherapy & Stem Cell Research 9 (2000) 161-173.

E. J. Woods, J. Liu, M. A. J. Zieger, J. R. T. Lakey, J. K. Critser, Water and cryoprotectant permeability characteristics of isolated human and canine pancreatic islets, Cell Transplantation 8 (1999) 549-559.

H. Yang, J. Acker, A. Chen, L. McGann, In situ assessment of cell viability, Cell Transplant 7 (1998) 443-451.

H. Yang, J. P. Acker, J. Hannon, H. Miszta-Lane, J. J. Akabutu, L. E. McGann, Damage and protection of UC blood cells during cryopreservation, Cytotherapy 3 (2001) 377-386.

H. Yang, Effects of incubation temperature and time after thawing on viability assessment of peripheral hematopoietic progenitor cells cryopreserved for transplantation, Bone Marrow Transplantation 32 (2003) 1021-1026.

H. Yang, H. Zhao, L. E. McGann, Effects of DMSO of flow cytometric absolute CD34+ cell enumeration, Cytotherapy 5 (2003) 453.

A. Zambelli, G. Poggi, G. Da Prada, P. Pedrazzoli, A. Cuomo, D. Miotti, C. Perotti, P. Preti, G. R. Della Cuna, Clinical toxicity of cryopreserved circulating progenitor cells infusion, Anticancer Research 18 (1998) 4705-4708.

M. A. J. Zieger, E. J. Woods, J. R. T. Lakey, J. Liu, J. K. Critser, Osmotic tolerance limits of canine pancreatic islets, Cell Transplantation 8 (1999) 277-284.

We claim:

1. A method for cryopreserving stem cells, the method comprising:

providing isolated stem cells in a serum-free liquid culture medium;

a. Cooling the stem cells to a first temperature between −5° C. and −15° C. and holding them for a first period of time between 1 and 30 minutes at said first temperature to generate ice outside of the stem cells; and thereafter b. Cooling the stem cells to a second temperature below −60° C. for storing the cells;

wherein steps a and b are carried out in the absence of a permeating cryopreservant.

2. The method of claim 1 in which the second temperature is at or above −196° C.

3. The method of claim 1 in which the second temperature is at or above the boiling temperature of liquid nitrogen.

4. The method of claim 1 carried out in the presence of a non-permeating cryopreservant.

\* \* \* \* \*